United States Patent
Hossack et al.

(10) Patent No.: US 9,526,922 B2
(45) Date of Patent: *Dec. 27, 2016

(54) SYSTEM FOR TREATMENT AND IMAGING USING ULTRASONIC ENERGY AND MICROBUBBLES AND RELATED METHOD THEREOF

(71) Applicant: University of Virginia Patent Foundation, Charlottesville, VA (US)

(72) Inventors: John A. Hossack, Charlottesville, VA (US); Brian R. Wamhoff, Charlottesville, VA (US); Alexander L. Klibanov, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,830

(22) Filed: Oct. 25, 2013

(65) Prior Publication Data

US 2014/0142468 A1 May 22, 2014

Related U.S. Application Data

(63) Continuation of application No. 12/739,128, filed as application No. PCT/US2008/081189 on Oct. 24, 2008, now Pat. No. 8,622,911.

(Continued)

(51) Int. Cl.
*A61K 41/00* (2006.01)
*A61N 7/00* (2006.01)
(Continued)

(52) U.S. Cl.
CPC . *A61N 7/00* (2013.01); *A61B 8/12* (2013.01); *A61B 8/445* (2013.01);
(Continued)

(58) Field of Classification Search
CPC ........... A61B 17/2202; A61B 2017/22088; A61B 2017/22089; A61B 8/12; A61B 8/445; A61B 8/481; A61K 41/0028; A61K 49/223; A61M 37/0092; A61N 7/00
(Continued)

(56) References Cited

U.S. PATENT DOCUMENTS 5,041,089 A 8/1991 Mueller et al.
5,117,831 A 6/1992 Jang et al.
(Continued)

FOREIGN PATENT DOCUMENTS

WO WO 2006/015091 A3 2/2006
WO WO 2006/015144 A1 2/2006
(Continued)

OTHER PUBLICATIONS

Stephens, DN et al. "Multi-frequency Array Development for Drug Delivery Therapies". 2006 IEEE Ultrasounics Symposium.*
(Continued)

*Primary Examiner* — Michael Rozanski
(74) *Attorney, Agent, or Firm* — Robert J. Decker; Alan W. Cannon

(57) ABSTRACT

A method and related system for providing therapy to a treatment site, such as stenosis or other vasculature disease, at one or more locations of a subject, such as the vasculature. The method includes: advancing an ultrasound catheter to or in proximity to the subject's treatment site; infusing microbubbles into or proximal to the treatment site; and delivering ultrasonic energy from the ultrasound catheter. The ultrasonic energy may be adapted for: imaging the treatment site, translating the microbubbles into or in the vicinity of the treatment site and/or rupturing the microbubbles.

28 Claims, 15 Drawing Sheets

Related U.S. Application Data

(60) Provisional application No. 61/000,632, filed on Oct. 26, 2007, provisional application No. 61/099,025, filed on Sep. 22, 2008.

(51) Int. Cl.
*A61K 49/22* (2006.01)
*A61B 17/22* (2006.01)
*A61B 8/12* (2006.01)
*A61M 37/00* (2006.01)
*A61B 8/00* (2006.01)
*A61B 8/08* (2006.01)

(52) U.S. Cl.
CPC ...... *A61B 17/2202* (2013.01); *A61K 41/0028* (2013.01); *A61K 49/223* (2013.01); *A61M 37/0092* (2013.01); *A61B 8/481* (2013.01); *A61B 2017/22088* (2013.01); *A61B 2017/22089* (2013.01)

(58) Field of Classification Search
USPC .................. 600/437, 439; 604/500; 424/9.52
See application file for complete search history.

(56) References Cited

U.S. PATENT DOCUMENTS

| | | | |
|---|---|---|---|
| 5,222,970 A | 6/1993 | Reeves et al. | |
| 5,415,634 A | 5/1995 | Glynn et al. | |
| 5,447,503 A | 9/1995 | Miller et al. | |
| 5,558,092 A | 9/1996 | Unger et al. | |
| 5,577,505 A | 11/1996 | Brock-Fisher et al. | |
| 5,707,354 A | 1/1998 | Salmon et al. | |
| 5,755,707 A | 5/1998 | Miyagawa et al. | |
| 5,770,222 A | 6/1998 | Unger et al. | |
| 5,827,171 A | 10/1998 | Dobak et al. | |
| 5,868,708 A | 2/1999 | Hart et al. | |
| 5,941,870 A | 8/1999 | Jang et al. | |
| 6,176,842 B1* | 1/2001 | Tachibana .......... | A61K 41/0047 604/101.03 |
| 6,352,683 B1 | 3/2002 | ten Cate | |
| 6,409,667 B1 | 6/2002 | Hossack | |
| 6,527,979 B2 | 3/2003 | Constantz et al. | |
| 6,565,601 B2 | 5/2003 | Wallace et al. | |
| 6,626,861 B1 | 9/2003 | Hart et al. | |
| 7,011,677 B2 | 3/2006 | Wallace et al. | |
| 7,078,015 B2 | 7/2006 | Unger | |
| 7,198,637 B2 | 4/2007 | Deshmukh et al. | |
| 7,341,569 B2 | 3/2008 | Soltani et al. | |
| 8,622,911 B2* | 1/2014 | Hossack et al. ............... | 600/439 |
| 9,237,898 B2* | 1/2016 | Hossack .................. | A61B 8/12 |
| 2002/0044907 A1 | 4/2002 | Constantz et al. | |
| 2002/0082680 A1 | 6/2002 | Shanley et al. | |
| 2002/0169496 A1 | 11/2002 | Wallace et al. | |
| 2003/0163192 A1 | 8/2003 | Wallace et al. | |
| 2003/0181973 A1 | 9/2003 | Sahota | |
| 2003/0199820 A1 | 10/2003 | Constantz et al. | |
| 2003/0204171 A1 | 10/2003 | Kucharczyk et al. | |
| 2003/0206960 A1 | 11/2003 | Eversen et al. | |
| 2003/0207907 A1 | 11/2003 | Eversen et al. | |
| 2003/0220666 A1 | 11/2003 | Mirigian et al. | |
| 2004/0030250 A1 | 2/2004 | Stewart | |
| 2004/0077948 A1 | 4/2004 | Violante et al. | |
| 2004/0111145 A1 | 6/2004 | Serino et al. | |
| 2004/0126400 A1 | 7/2004 | Iversen et al. | |
| 2004/0158308 A1 | 8/2004 | Hogendijk et al. | |
| 2004/0236414 A1 | 11/2004 | Brar et al. | |
| 2004/0254635 A1 | 12/2004 | Shanley et al. | |
| 2005/0017725 A1 | 1/2005 | Murakami et al. | |
| 2005/0084538 A1 | 4/2005 | Dayton et al. | |
| 2005/0192556 A1 | 9/2005 | Soltani et al. | |
| 2006/0005876 A1 | 1/2006 | Gaudiana et al. | |
| 2006/0078501 A1 | 4/2006 | Goertz et al. | |
| 2006/0161103 A1 | 7/2006 | Constantz et al. | |
| 2006/0189928 A1 | 8/2006 | Camus et al. | |
| 2006/0235501 A1 | 10/2006 | Igaki et al. | |
| 2007/0003528 A1 | 1/2007 | Consigny et al. | |
| 2007/0010577 A1 | 1/2007 | Lanza et al. | |
| 2007/0043389 A1 | 2/2007 | Shindelman et al. | |
| 2007/0049867 A1 | 3/2007 | Shindelman et al. | |
| 2007/0055132 A1 | 3/2007 | Camus et al. | |
| 2007/0055327 A1 | 3/2007 | Esch et al. | |
| 2007/0071683 A1 | 3/2007 | Dayton et al. | |
| 2008/0103443 A1 | 5/2008 | Kabrick et al. | |
| 2008/0243233 A1 | 10/2008 | Ben-Muvhar et al. | |
| 2016/0206867 A1* | 7/2016 | Hossack .................. | A61B 8/12 |

FOREIGN PATENT DOCUMENTS

| | | |
|---|---|---|
| WO | WO 2006/089243 A3 | 8/2006 |
| WO | WO 2008/057626 A3 | 5/2008 |
| WO | WO 2008/112870 A3 | 9/2008 |
| WO | WO 2008/115745 A3 | 9/2008 |
| WO | WO 2008/118737 A1 | 10/2008 |

OTHER PUBLICATIONS

Thorn, T., et al., Heart disease and stroke statistics—2006 update: a report from the American Heart Association Statistics Committee and Stroke Statistics Subcommittee. Circulation, 2006. 113(6): p. e85-e151.

Kandzari, D. E., et al., Frequency, Predictors, and Outcomes of Drug-Eluting Stent Utilization in Patients With High-Risk Non-ST-Segment Elevation Acute Coronary Syndromes, the American Journal of Cardiology, 2005. 96(6): p. 750-755.

Rao, S.V., et al., On-Versus Off-Label Use of Drug-Eluting Coronary Stents in Clinical Practice (Report from the American College of Cardiology National Cardiovascular Data Registry [NCDR]). The American Journal of Cardiology, 2006. 97(10): p. 1478-1481.

FDA, Circulatory Systems Devices Advisory Panel, Dec. 7, 2006. Transcript:]rtiygi//w.

Hendrix, J., et al., 5' CArG degeneracy in smooth muscle falphaj-actin is required for injury-induced gene suppression in vivo. J. Clin. Invest., 2005. 115(2): p. 418-427.

McDonald, O., et al., Control of SRF binding to CArG box chromatin regulates smooth muscle gene expression in vivo. J. Clin. Invest., 2006. 116(1): p. 36-48.

Owens, G., M. Kumar, and B. Wamhoff, Molecular Regulation of Vascular Smooth Muscle Cell Differentiation in Development and Disease. Physiol. Rev., 2004. 84(3): p. 767-801.

Wamhoff, B., et al., L-type Voltage-Gated Ca2+ Channels Modulate Expression of Smooth Muscle Differentiation Marker Genes via a Rho Kinase/Myocardin/SRF-Dependent Mechanism. Circulation Research, 2004. 95(4): p. 406-414.

Braun, M., et al., Cellular adhesion molecules on vascular smooth muscle cells. Cardiovascular Research, 1999. 41(2): p. 395-401.

Braun-Dullaeus, R., et al., Cell cycle-dependent regulation of smooth muscle cell activation. Arterioscler Thromb Vase Biol, 2004. 24: 845-850, 2004: p. 845-850.

Landry, D., et al., Activation of the NF-kappa B and I kappa B system in smooth muscle cells after rat arterial injury. Induction of vascular cell adhesion molecule-1 and monocyte chemoattractant protein-1. Am J Pathol, 1997. 151(4): p. 1085-1095.

Parry, T., et al., Drug-eluting stents: sirolimus and paclitaxel differentially affect cultured cells and injured arteries. Eur J Pharmacol, 2005. 524(1-3): p. 19-29.

Wessely, R., A. Schomig, and A. Kastrati, Sirolimus and Paclitaxel on Polymer-Based Drug-Eluting Stents: Similar But Different. Journal of the American College of Cardiology, 2006. 47(4): p. 708-714.

Webster, A., et al., Target of rapamycin inhibitors (sirolimus and everolimus) for primary immunosuppression of kidney transplant recipients: a systematic review and meta-analysis of randomized trials. Transplantation, 2006. 81(9): p. 1234-1248.

Ross, R., The pathogenesis of atherosclerosis: a perspective for the 1990s. Nature, 1993. 362: p. 801-809.

(56) References Cited

OTHER PUBLICATIONS

Denger, T. and T. Pober, Cellular and molecular biology of cardiac transplant rejection. Journal of Nuclear Cardiology, 2000. 7: p. 669-685.
Sheridan, F., P. Cole, and D. Ramage, Leukocyte adhesion to the coronarymicrovasculature during ischemia and reperfusion in an in vivo canine model. Circulation, 1996. 93: p. 1784-1787.
Villanueva, F., A. Klibanov, and W. Wagner, Microbubble-endothelial cell interactions as a basis for assessing endothelial function. Echocardiography, 2002. 19: p. 427-438.
Klibanov, A.L., Targeted Delivery of Gas-Filled Microspheres, Contrast Agents for Ultrasound Imaging. Advanced Drug Delivery Reviews, 1999. 37: p. 139-157.
Klibanov, A., et al., Targeted ultrasound contrast agent for molecular imaging of inflammation in high-shear flow. Contrast Media and Molecular Imaging, 2006. 1(6): p. 259-266.
Rosenschein, U., et al., Ultrasound Imaging-Guided Noninvasive Ultrasound Thrombolysis. Circulation, 2000. 102: p. 238-245.
Chan, An image-guided high intensity focused ultrasound device for uterine fibroids treatment. Medical Physics, 2002. 29(11): p. 2611-2620.
Vaezy, S., et al., Ultrasound image-guided therapy. Academic Radiology, 2003. 10(8): p. 956.
Vaezy, S., et al., High intensity focused ultrasound for hemostasis of femoral artery catheter wounds. Ultrasound in Medicine and Biology, 2006. 32(5 Supplement 1): p. 100.
Crum, L., Guided High Intensity Focused Ultrasound (HIFU) for Mission—Critical Care, 2004 p. 1-4.
Bouakaz, A., F. Cate, and N. de Jong, A new ultrasonic transducer for improved contrast nonlinear imaging. Physics in Medicine & Biology, 2004. 49(16): p. 3515-3525.
Forsberg, F., et al., Design and acoustic characterization of a multi-frequency harmonic array for nonlinear contrast imaging. Proceeding of 2001 IEEE Ultrasonics Symposium, 2001.2: p. 1721-1724.
Rychak, J. A. Klibanov, and J. Hossack, Acoustic Radiation Force Enhances Targeted Delivery of Ultrasound Contrast . Microbubbles: in vitro Verification. IEEE Transactions on Ultrasonics Ferroelectrics & Frequency Control, 2005. 52(3): p. 421-433.
Marx, S., et al., Rapamycin-FKBP Inhibits Cell Cycle Regulators of Proliferation in Vascular Smooth Muscle Cells. Circulation Research, 1995. 76(3): p. 412-417.
Klibanov, A., et al., Klibanov, A., et al., Attachment ofligands to gas-filled microbubbles via PEG spacer and lipid residues anchored at the interface. Proc. Intl. Symp. Control. Rel. Bioact. Mat., 1999. 26: p. 124-125.
Wilson, T., et al., The ultrasonix 500RP: A commercial ultrasound research interface. IEEE Transactions Ultrasonics, Ferroelectrics and Frequency Control, 2006. 53(10): p. 1772-1782.
Takalkar, A., et al., Binding and detachment dynamics of microbubbles targeted to P-selectin under controlled shear flow. Journal of Controlled Release, 2004. 96(3): p. 473-482.
Klibanov, A., et al., Detection of individual microbubbles of an ultrasound contrast agent: fundamental and pulse inversion imaging. nversion maging. Academic Radiology, 2002: p. S279-S281.
Jayaweera, A., et al., In vivo myocardial kinetics of air-filled albumin microbubbles during myocardial contrast echocardiography. Comparison with radiolabeled red blood cells. Circulation Research, 1994. 74(6): p. 1157-1165.
Springer, T., Adhesion receptors of the immune system. Nature, 1990. 347: p. 425-434.
Dayton, P., et al., Acoustic radiation force in vivo: a mechanism to assist targeting of microbubbles. Ultrasound in Medicine & Biology, 1999. 25(8): p. 1195-1201.
Fowlkes, J., et al., The role of acoustic radiation force in contrast enhancement techniques using bubble-based ultrasound contrast agents. Journal of the Acoustical Society of America, 1993. 93: p. 2348.
Zhao, S., et al., Radiation force assisted targeting facilitates ultrasonic molecular imaging. Molecular Imaging, 2004. 3: p. 1-14.
Shortencarier, J., et al., A method for radiation-force localized drug delivery using gas-filled liposheres. IEEE Trans. Ultrasonics, Ferroelectrics and Frequency Control, 2004. 51: p. 822-831.
Dayton, P., et al., A preliminary evaluation of the effects of primary and secondary radiation forces on acoustic contrast agents. IEEE Transactions on Ultrasonics Ferroelectrics & Frequency Control, 1997. 44(6): p. 1264-1277.
Dayton, P., J. Allen, and K. Ferrara, The magnitude of radiation force on ultrasound contrast agents. Journal of the Acoustical Society of America, 2002. 112: p. 2183- 2192.
Bosse, R. and D. Vestweber, Only simultaneous blocking of the L- and P-selectin completely inhibits neutrophil migration into mouse peritoneum. European Journal of Immunology, 1994. 24: p. 3019-3024.
Lindner, J., et al., Ultrasound Assessment of Inflammation and Renal Tissue Injury With Microbubbles Targeted to P-Selectin. Circulation, 2001. 104(17): p. 2107-2112.
Burns, P., S. Wilson, and D. Simpson, Pulse inversion imaging of liver blood flow: improved method for characterizing focal masses with microbubble contrast. Invest Radiol, 2000. 35(1): p. 71.
Phillips, P., Contrast Pulse Sequences (CPS): Imaging non-linear microbubbles. Proceedings of the 2001 IEEE Ultrasonics Symposium, 2001. 2: p. 1739-1745.
Unger, E., et al., Acoustically active liposheres containing paclitaxel—A new therapeutic ultrasound contrast agent. Investigative Radiology, 1998. 33: p. 886-892.
Boudennaia, T.Y. and KX. Napoli, Validation of a practical liquid chomatography with ultraviolet detection method for quantification of whole-blood everolimus in a clinical TDM laboratory. Therapeutic Drug Monitoring, 2005. 27(2): p. 171-177.
FDA, Circulatory Systems Devices Advisory Panel, Dec. 8, 2006. Transcript:]rtiygi//w.
Klibanov, A., et al., Polymeric sialyl Lewis X microbubbles: targeted ultrasound contrast agents for molecular imaging of inflammation. RSNA Abstract Book, 2006(Abs. # SSK06-06): p. 436-437.
Price, et al., Delivery of Colloidal Particles and Red Blood Cell to Tissue Through Microvessel Ruptures Created by Targeted Microbuble Destruction with Ultrasound. 1998, 98, No. 13, pp. 1264-1267.
Reference citations cited in Office Action in EP 08841415.6-1659 on Nov. 11, 2016.

* cited by examiner

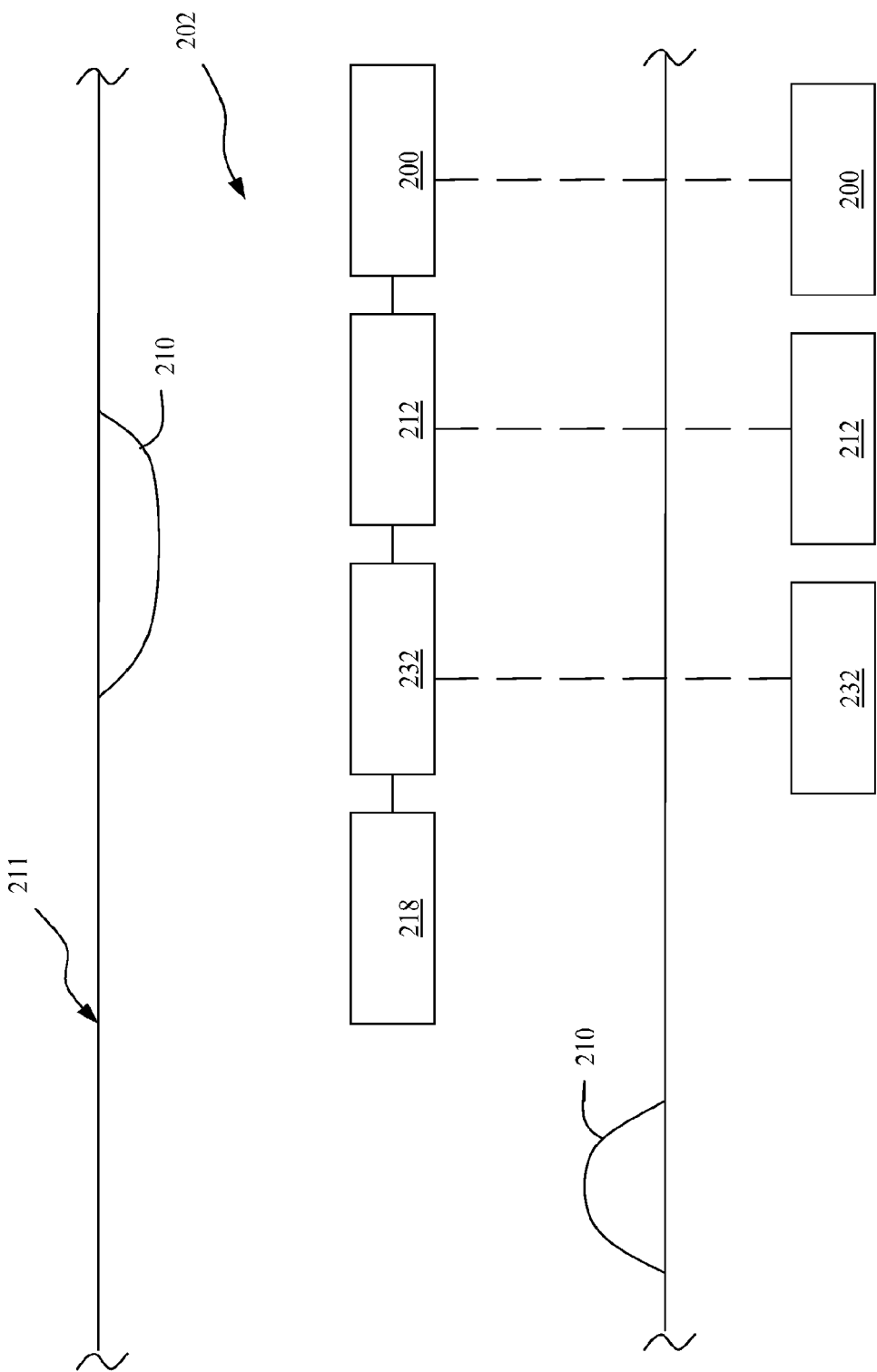

Balloon occluder upstream and downstream of bubble port and ultrasound transducer(s)

SYSTEM FOR TREATMENT AND IMAGING USING ULTRASONIC ENERGY AND MICROBUBBLES AND RELATED METHOD THEREOF

RELATED APPLICATIONS

The present application is a continuation of Application Ser. No. 12/739,128, filed Aug. 9, 2010, now U.S. Pat. No. 8,622,911, which is an application filed under 35 U.S.C. 371 claiming priority to International Application PCT/US2008/081189, filed Oct. 24, 2008, which claims priority to U.S. Provisional Application Ser. No. 61/000,632, filed Oct. 26, 2007, entitled "Molecular Targeted Microbubbles for Enhanced Blood Vessel Imaging and Therapeutic Treatment of Neointimal Hyperplasia;" and U.S. Provisional Application Ser. No. 61/099,025, filed Sep. 22, 2008, entitled "Molecular Targeted Microbubbles for Enhanced Blood Vessel Imaging and Therapeutic Treatment of Neointimal Hyperplasia". Each of application Ser. No. 12/739,128; International Application PCT/US2008/081189; U.S. Provisional Application Ser. No. 61/000,632 and U.S. Provisional Application Ser. No. 61/099,025 is hereby incorporated herein, in its entirety, by reference thereto.

GOVERNMENT SUPPORT

Work described herein was supported by Federal Grant No. 5R01EB002185-07, awarded by the NIH. The Government has certain rights in the invention.

BACKGROUND OF THE INVENTION

Cardiovascular disease (CVD) was blamed for 37% of the 2.4M deaths in the US (2003) [1]. CVD is the leading cause of death in the US and the developed world.

Currently Available Drug-Eluting Stents (DES) Pose a Major Potential Health Concern The clinical use of Drug Eluting Stents (DES), in relation to Bare Metal Stents (BMS), has evolved over a period of approximately 18 months from approximately 0% usage in the U.S., to the point where they were used in approximately 80% of coronary stent procedures in the U.S. [2, 3].

The above cited recent studies indicates that there is a significant, growing population (approximately 6 Million individuals worldwide [4]) who currently find themselves having been implanted with DES and face a choice between taking the expensive and risky drug clopidogrel—potentially for life—or increased risk of premature death.

The Vascular Smooth Muscle Cell, VCAM-1 and Rapamycin: Vascular SMC Proliferation Contributes to Angioplasty-Induced Stenosis and in-Stent Restenosis.

The primary function of the vascular SMC in adult animals is contraction and SMCs express a unique repertoire of genes that allow for this specialized form of contraction, including SM α-actin, smooth muscle myosin heavy chain (SMMHC), SM22α, calponin, desmin, smoothelin—genes we refer to as SMC differentiation marker genes [5-8]. This repertoire of genes is typically used to describe the "contractile" phenotype or mature SMC.

VCAM-1 is a Marker of the Phenotypically Modified/Proliferating SMC.

The changes in SMC gene expression profiles associated with injury-induced phenotypic modulation are transient. That is, SMCs undergo phenotypic modulation as a natural response to repair the injured blood vessel, transitioning from a contractile phenotype to a synthetic phenotype but revert back to a contractile phenotype as the lesion resolves itself. Thus, this continuum of altered SMC gene expression profiles can be used to target the phenotypically modified SMC that invests in the developing neointima using molecular targeting. VCAM-1 (vascular cell adhesion molecule 1) is expressed in proliferating SMCs [9, 10] and transiently upregulated in SMCs following acute vascular injury and in atherosclerotic lesions [11]. The function of VCAM-1 is to promote cell-cell interaction required for SMC migration and recruitment or attraction of other cell types into the lesion, e.g. VCAM-1 interaction on SMCs with integrins on leukocytes, monocytes or macrophages (all inflammatory cells) [9]. Because VCAM-1 is expressed at much lower levels in the quiescent contractile SMC phenotype, but increased in proliferating SMCs, VCAM-1 can thus be used to target the proliferating SMC.

Rapamycin is a Potent SMC Anti-Proliferative Agent and the Bench-Mark Agent for Preventing in-Stent Restenosis by Release from a DES.

The cell cycle consists of 5 basic steps: dormancy (G0) or the contractile SMC phenotype, gap phase 1 (G1), synthesis (S), pre-mitosis or gap phase 2 (G2) and mitosis (M). In response to acute vascular injury, SMCs leave G0 and enter G1 to begin the process of cell proliferation and division into M phase; this is the synthetic migratory or proliferative SMC phenotype. The strategies for preventing SMC proliferation and entry into the cell cycle have been to block various phases of the cell cycle once the cell has left G0 in response to injury or some acute growth stimulus. Sirolimus, or rapamycin, and its analogues, ABT578 (Abbot Pharmaceuticals) and everolimus, are immunosuppressants with both anti-inflammatory and antiproliferative properties that interfere early in the cell cycle by inhibiting the passage of cells from G1 to S phase. Drugs that inhibit cell cycle in the G1 phase are considered cytostatic and may be less toxic than drugs that act later in the cell cycle [12, 13]. Rapamycin is the most thoroughly investigated agent of this group and has become the bench-mark agent for the prevention of coronary artery restenosis [14]. Thus, because rapamycin is considered "cytostatic", SMCs treated with rapamycin do not die but maintain their viability in the growth arrested state.

Molecular Targeting of Microbubble Carriers

Recent research has investigated the feasibility of targeted ultrasound contrast microbubbles as a means of detecting intravascular manifestations of disease. Pathology is often accompanied by alterations of the endothelial cell layer lining of the affected blood vessels. This dysfunction may occur in the microcirculation, and is identified by the selective expression or up-regulation of certain molecules on the vascular endothelial surface. Many of the molecular markers of endothelial dysfunction corresponding to disease states such as atherosclerosis [15], transplant rejection [16], inflammation and ischemia reperfusion injury [17] are well characterized. However, there is currently no non-invasive, clinically approved technique to assess the extent and location of such vascular pathologies. Experimental formulations of targeted microbubbles, which contain a surface-bound ligand specific for the intended target, are injected intravascularly and, after a short circulation period, are observed to accumulate at the target site. Subsequent ultrasound imaging enables determination of the location and extent of the targeted disease state [18]. This technique, known as "targeted contrast enhanced ultrasound", may achieve high spatial resolution, real time imaging, and a linear or other measurable correlation between adherent microbubbles and the received signal.

There is therefore a need for, among other things, the drug, the drug carrier, and the means of localizing delivery; and a means to guide the focal delivery under real time image guidance.

SUMMARY OF THE INVENTION

There is a need for real time, noninvasive, imaging method to reliably guide the focal delivery of antiproliferative drug to regions at risk of restenosis following angioplasty and/or stenting.

An aspect of some of the various embodiments of the invention comprise an ultrasound contrast agent that have a selected drug incorporated into the bubble shell. In one embodiment, the drug may be rapamycin. It should be appreciated that the present invention is not limited to any particular drug or class of drug, or agent (or any other type of medium or material being delivered to the location of the subject or the treatment site or diagnostic site of the subject. An aspect of various embodiments of the present invention may further comprise the means (a transducer [or transducer array] and its associated driving electronics) to deliver ultrasound energy ("therapeutic") to break the bubbles in such a manner as to focally deliver drug material to selected local cells. For example, but not limited thereto, the selected cells are those on or in the wall of a selected blood vessel. The precise mechanisms and the optimal conditions for ultrasound mediated drug delivery are heretofore not well understood. What is known from extensive literature is that the combination of bubbles plus ultrasound greatly improve the delivery of drug (or gene) material through the cell membrane. In an approach, the "therapeutic" ultrasound transducer is intimately integrated with an "imaging" ultrasound transducer that provides real-time, noninvasive imaging for guiding the precise delivery of potent drugs to a selected tissue region. Similar transducers used clinically are referred to as intravascular ultrasound (IVUS) catheters. Typically, the design of an optimal imaging transducer and an optimal therapeutic transducer are different—e.g. the therapeutic transducer may operate in a high power transmit mode of about 0.5 to about 2 MHz, whereas the imaging transducer operates as a finely sampled imaging array about 5 to about 30 MHz range. It should be appreciated that other higher and lower frequency modes may, of course, be employed within the context of the invention as desired or required. Nevertheless, it is possible to make compromises in the transducer design and arrive at a common design for both imaging and therapeutic effect.

The combined transducer may be catheter-based, may transthoracically-based (i.e. "conventional" diagnostic ultrasound) and intravascularly, as is the case with IVUS—introduced through femoral or carotid artery. The transducer may also be introduced via any natural or synthetic body cavity/orifice (uretha, anus, vagina, mouth/esophagus or surgical incision in any body part). Transducer designs (or aspects thereof) for some of these applications or aspects of the applications may be known in context of conventional diagnostic ultrasound and most large vendors develop and market transducers for each of these applications.

The drug/contrast may be delivered systemically via intravenous (IV) injection or it may be delivered more locally such as from an aperture/conduit in a catheter placed into the veinous or arterial circulatory system.

The drug may exist "side by side" with the agent—i.e. the drug not bound into the bubble shell. When the drug is injected "side by side" it may be dissolved in any suitable solvent appropriate for that drug (e.g. water, lipid, alcohol, or solid form-for example, in very fine particle form—like nanoparticle, etc. Moreover, the drug could be in a gas or solid, for example, could be in the core or shell of the bubble (respectively)); in addition to being in the liquid phase, the drug may be used in the solid dosage forms, such as in nanoparticle formulations of kinds familiar to those skilled in the art.

The bubbles may be molecular targeted to enhance cell-specific selectivity—per the techniques, for example, described in the multiple papers by Klibanov [19, 20] and colleagues.

An aspect(s) of various embodiments of the present invention may be provide a number of novel and nonobvious features, elements and characteristics, such as but not limited thereto, the following: integrated image guidance of ultrasound-based local drug delivery; integrated image guidance of ultrasound-based local gene delivery; cell-specific molecular targeting of therapeutic agent; and ultrasound imaging-based estimation of the delivery of therapeutic agent.

An aspect of an embodiment or partial embodiment of the present invention (or combinations of various embodiments in whole or in part of the present invention) comprises a method of providing therapy to a treatment site at one or more locations of a subject. The method comprising: advancing an ultrasound catheter to or in proximity to the subject's treatment site, the catheter having a proximal region and distal region; infusing microbubbles from the distal region of the ultrasound catheter into or proximal to the treatment site; and delivering ultrasonic energy from the distal region of the ultrasound catheter. The ultrasonic energy adapted for: imaging the treatment site and rupturing the microbubbles. The ultrasonic energy may also adapted for translating the microbubbles.

An aspect of an embodiment or partial embodiment of the present invention (or combinations of various embodiments in whole or in part of the present invention) comprises an ultrasound catheter system for providing therapy to a treatment site at one or more locations of a subject. The system comprising: a tubular member having a proximal region and distal region, the proximal end of the ultrasound catheter adapted to advance to or in proximity to the subject's treatment site; a microbubble reservoir in hydraulic communication with the tubular member, the microbubble reservoir is adapted to release microbubbles that are intended to be located into or proximal to the treatment site; an ultrasonic energy source in communication with the distal region of the tubular member. The ultrasonic energy adapted for: imaging the treatment site and rupturing the microbubbles. The system further comprises a control circuitry configured to send electrical activation to the ultrasonic energy source. The ultrasonic energy may also adapted for translating the microbubbles.

A method and related system for providing therapy to a treatment site, such as stenosis or other vasculature disease, at one or more locations of a subject, such as the vasculature. The method includes: advancing an ultrasound catheter to or in proximity to the subject's treatment site; infusing microbubbles into or proximal to the treatment site; and delivering ultrasonic energy from the ultrasound catheter. The ultrasonic energy may be adapted for: imaging the treatment site, translating the microbubbles into or in the vicinity of the treatment site and/or rupturing the microbubbles.

These and other objects, along with advantages and features of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, and serve to explain the principles of the invention. The drawings are provided only for the purpose of illustrating select embodiments of the invention and are not to be construed as limiting the invention.

FIGS. 2(A)-(C) schematically illustrate various embodiments (or partial embodiments) of the present invention ultrasound catheter system for providing therapy (and/or diagnosis) to a treatment site at one or more locations of a subject.

FIG. 8 illustrates: at FIG. 8(A) a low frequency layer pulse-echo response; at FIG. 8(B) an Experimental high frequency pulse-echo response; at FIG. 8(C) an experimental high frequency pulse echo response after inverse filtering; and at FIG. 8(D) an FEA simulation of proposed, improved (better acoustic matching) high frequency layer design (without filtering) All plots are voltage echo response vs. time (μs)

DETAILED DESCRIPTION OF THE INVENTION

Figure 1:
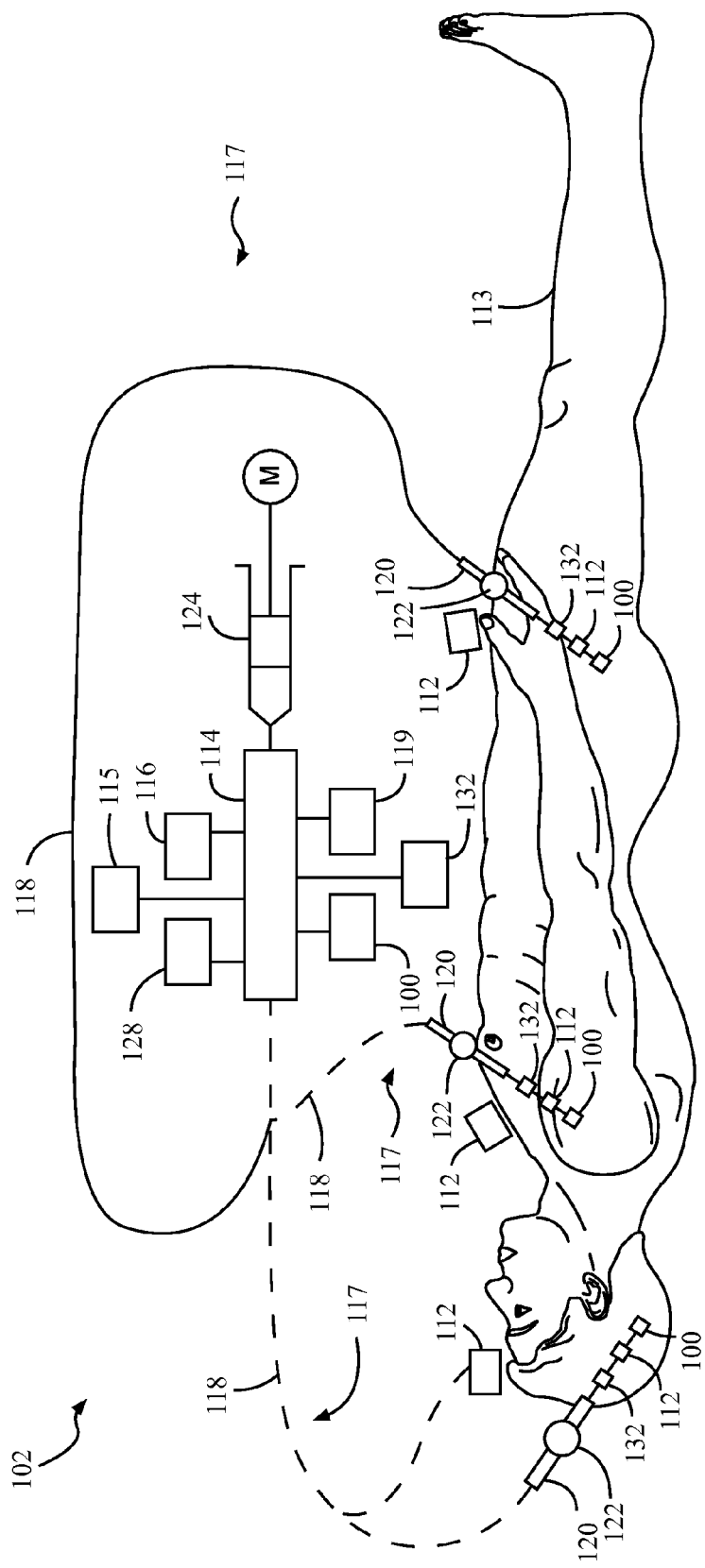
FIG. 1 provide a schematic illustration of an embodiment (or partial embodiment) of the present invention ultrasound catheter system 102 for providing therapy (and/or diagnosis) to a treatment site at one or more locations of a subject.

FIG. 1 provides a schematic illustration of an embodiment (or partial embodiment) of the present invention ultrasound catheter system 102 for providing therapy to a treatment site at one or more locations of a subject. The system 102 may comprise a tubular member 118 such as a catheter or multiple catheters. The catheter(s) 118 having a proximal region 115 and distal region 117, whereby the proximal end of the ultrasound catheter is adapted or configured to be advanced to or in proximity to the subject's treatment site. It should be appreciated that any one of the catheters as shown may be a plurality of catheters and any given catheter may have one or more lumens or channels therein. The system further comprises a microbubble reservoir 132 in hydraulic communication with the tubular member. The microbubble reservoir is 132 may be located in the proximal region 115 and/or the proximal region 117 as desired or required. The microbubble reservoir is 132 may be adapted to release microbubbles that are intended to be located into or proximal to the treatment site. The system further comprises an ultrasonic energy 112 source in communication with the proximal region 115 and/or distal region 117 of the tubular member 118. The ultrasonic energy 112 may be capable of: imaging the treatment site, and/or rupturing the microbubbles. The ultrasonic energy 112 may be located outside or at least partially surrounding the subject 113 or patient. The system further comprises a control circuitry 100 or controller configured to send electrical activation to the ultrasonic energy source 112 or any components or subsystem affiliated with the catheter system 102. Further, the ultrasonic energy source 112 may provide ultrasonic radiation forces for translating the microbubbles into or in the vicinity of the treatment site; or alternatively the mechanical forces may be provided for translating the microbubbles into or in the vicinity of the treatment site, as well as a combination of both mechanical and ultrasonic forces (acoustic wave) to achieve the desired or required result.

The tubular member 118 and other components and subsystems affiliated with the catheter system 102 may be manufactured in accordance with a variety of techniques known to an ordinarily skilled artisan. Suitable materials and dimensions can be readily selected based on the natural and anatomical dimension of the treatment or diagnosis site and on desired percutaneous access site or exterior.

For example, in an exemplary embodiment, the tubular body proximal region 115 and/or distal region 117 comprises a material that has sufficient flexibility, kink resistance, rigidity and structural support to push the ultrasound energy source 112 through the patient's vasculature or organ to a treatment site or vicinity thereof. Examples of such materials include, but are not limited to, extruded polytetrafluoroethylene ("PTFE"), polyethylenes ("PE"), Pebax—made by Arkema, polyamides and other similar materials. I n certain embodiments, the tubular body proximal region 115 and/or distal region 117 is reinforced by braiding, mesh or other constructions to provide increased kink resistance and ability to be pushed. For example, nickel titanium or stainless steel wires can be placed along or incorporated into the tubular member or body 118 to reduce kinking. For example, various guidewires, sheaths and additional tubular members may be implemented to handle the communications, navigations, controlling and imaging, etc.

It should be appreciated that the aforementioned catheter device, reservoir, ultrasound, and controller may be disposed entirely inside the applicable location of the subject as desired or required, outside the location of the subject as desired or required or a combination of inside or outside the location of the subject. The one or more locations of the subject may be an organ. The organ may include hollow organs, solid organs, parenchymal tissue, stromal tissue, and/or ducts. The one or more locations of the subject may be a tubular anatomical structure. The tubular anatomical structure may be a blood vessel. Further, for example, the treatment site may be a vasculature treatment site comprising at least one of the following: stenosis region or any region exhibiting vascular disease.

In an approach, a manifold and/or axis port 114 couples several therapeutic and/or diagnostic devices typified by device 116 to the catheter system 102. A syringe, flow-driver or pumping device 124 is also in communication with the manifold 114. The catheter system 102 in turn may be delivered through a guide sheath 120 that may be in communication with a navigation guide 122. In operation the physician or user inserts one or more such catheter system 102 into the body of the subject 113, for instance on going into the leg, chest or skull (or other anatomical part or parts or subject region or regions to cover the hollow or solid organs, blood vessels, etc.) under imaging guidance or other applicable examination or intervention. The same or similar ultrasound visualization may be used to follow the progress of the one or more implant(s) both acutely and chronically. This catheter device may have various interior and peripheral lumens, chambers and channels. Such interior and peripheral lumens, chambers and channels may be used to deliver other devices and perform various diagnostic functions. For example, each lumen, chamber, and channel may communicate with a separate port of the manifold 114. A lumen, chamber or channel may contain a pressure transducer 128. Other lumens and channels may be devoted to an optical or other type of cell counter device, for example, as shown generically as device 119 in FIG. 1. Such a device may operate with two optical fibers (optical device or counter) located in two separate lumens and/or ports to measure the number of and viability of cells, agents, drugs or microbubbles delivered by the catheter. An example of fiber optics related application/technology is discussed in U.S. patent application Ser. No. 10/444,884, filed May 23, 2003 (U.S. Application No. 2003/0204171, published Oct. 30, 2003), and of which are hereby incorporated by reference herein in their entirety.

It should be appreciated that many other embodiments of controller, catheter system, ultrasound energy source(s), manifold and/or axis port, proximal region, therapeutic and/or diagnostic devices, distal region, tubular member, other lumen(s), pressure transducer, microbubble reservoir, microbubble propeller or microbubble translator or propeller, flow channeling and recirculation means, microcoil means, pump means, pressure and flow-rate monitor means, imaging means, computer means, drug-eluting stents (DES), and other details of construction and use constitute non-inventive variations of the novel and insightful conceptual means, system, and technique which underlie the present invention. An example of systems and methods that may be implemented with various embodiments of the present invention are provided in the following commonly owned applications: U.S. patent application Ser. No. 10/444,884, filed May 23, 2003 (US Application No. 2003/0204171, published Oct. 30, 2003); PCT Application No. PCT/US2005/026738, filed Jul. 28, 2005; and PCT Application No. 2006/005876, filed Feb. 16, 2006, and of which are hereby incorporated by reference herein in their entirety.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

Figure 2B:
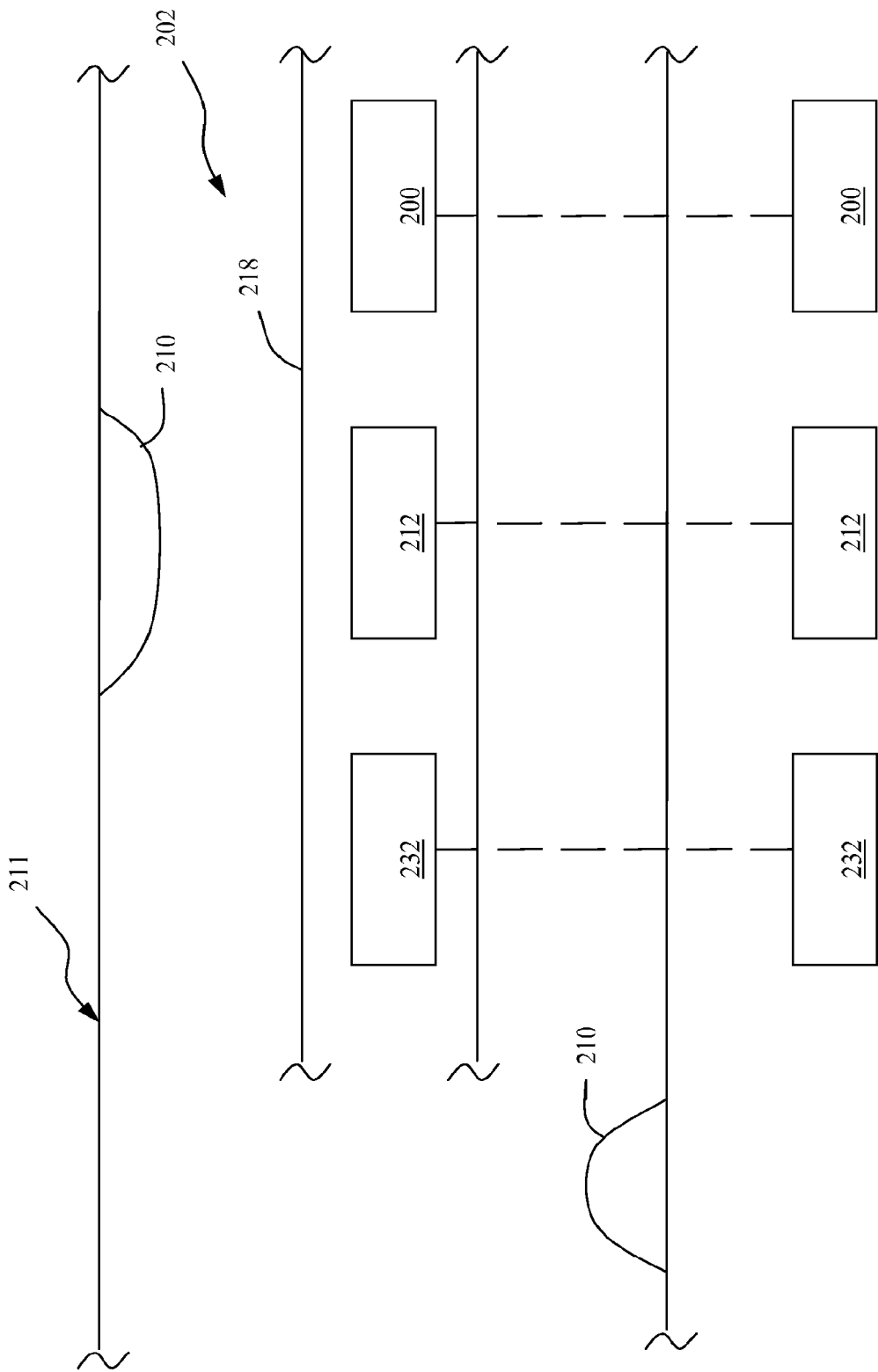
Figure 2C:
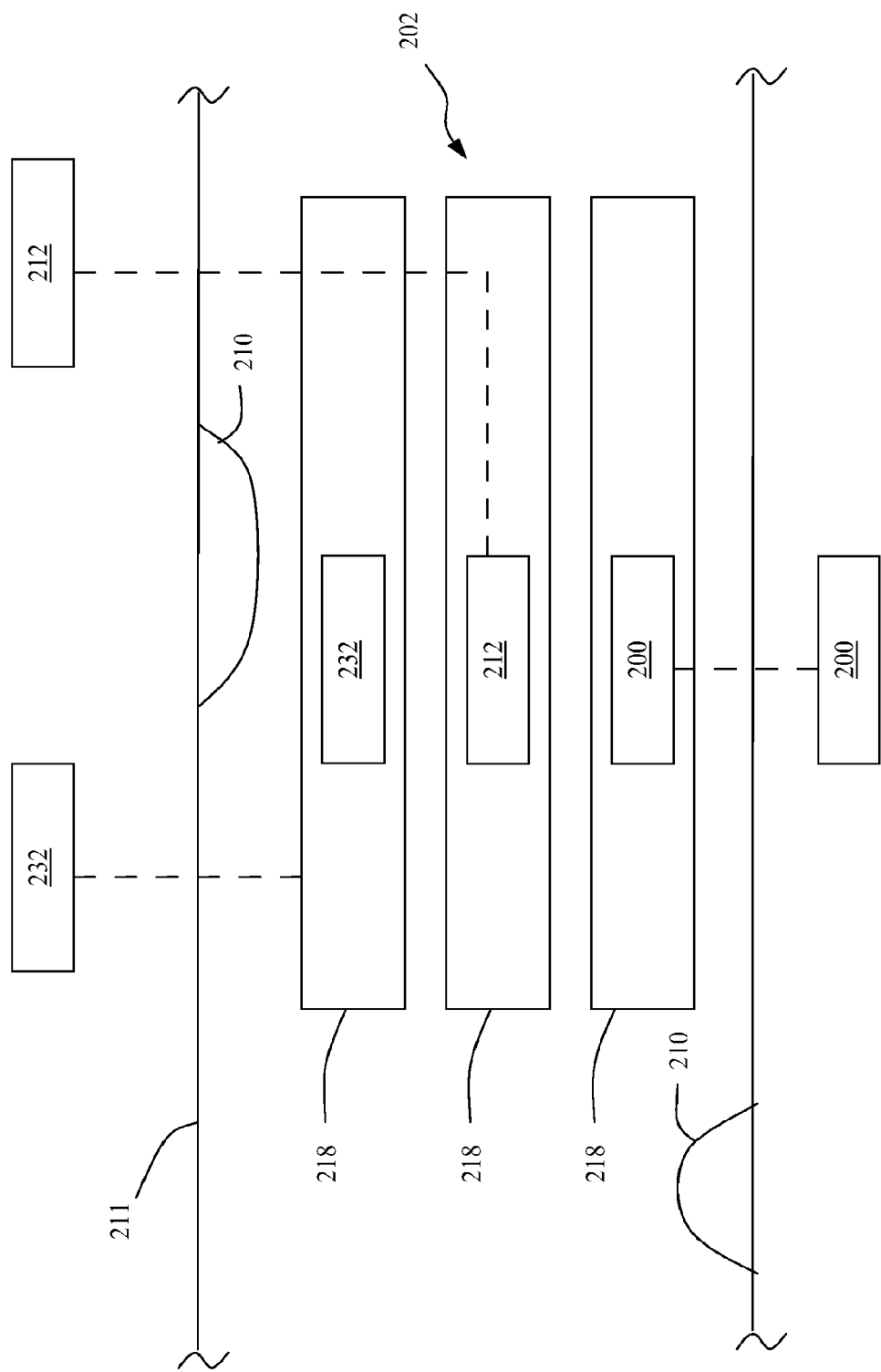

FIGS. 2(A)-(C) schematically illustrate various embodiments (or partial embodiments) of the present invention ultrasound catheter system for providing therapy to a treatment site at one or more locations of a subject. The catheter system 202 may comprise a tubular member 218 such as a catheter or multiple catheters. The catheter(s) having a proximal region and distal region, whereby the proximal end of the ultrasound catheter is adapted or configured to be advanced to or in proximity to the subject's treatment site. It should be appreciated that any one of the catheters 218 as shown may be a plurality of catheters and any given catheter may have one or more lumens therein. The system further comprises a microbubble reservoir 232 in hydraulic communication with the tubular member 218 and any lumens, channels, controllers or communication devices. The microbubble reservoir 232 is adapted to release microbubbles that are intended to be located into or proximal to the treatment site 210 at the desired or applicable location 211 of the subject. The system 202 further comprises an ultrasonic energy source 212 in communication with the distal region (or other region as desired or required) of the tubular member 218 (or other components or subsystems of the present invention). The ultrasonic energy is adapted for or capable of: imaging the treatment site 210, and rupturing the microbubbles. The system 202 further comprises a control circuitry 200 configured to send electrical activation to the ultrasonic energy source 212, as well as other components and subsystems of the present invention. Further, the ultrasonic energy source 212 may provide ultrasonic radiation forces for translating the microbubbles into or in the vicinity of the treatment site 210 at the desired or applicable location 211 of the subject; or alternatively the mechanical forces may be provided for translating the microbubbles into or in the vicinity of the treatment site 210, as well as a combination of both mechanical and ultrasonic forces (acoustic wave) to achieve the desired or required result.

It should be appreciated that the aforementioned catheter 218, reservoir 232, ultrasound 212, and controller 200 may be disposed entirely inside the applicable location of the subject, outside the location of the subject or a combination of inside or outside the location of the subject. The one or more locations 211 of the subject may be an organ. The organ may include hollow organs, solid organs, parenchymal tissue, stromal tissue, and/or ducts. The one or more locations 211 of the subject may be a tubular anatomical structure. The tubular anatomical structure may be a blood vessel. Further, for example, the treatment site 210 may be a vasculature treatment site comprising at least on of the following: stenosis region or any region exhibiting vascular disease. Further, for example, the treatment site 210 may be a vasculature treatment site and/or a diagnostic site.

Development of Transducer/Instrumentation to Optimize Delivery of a Therapeutic Agent by Microbubble Carrier.

Spatially localized, focused, non-invasive/minimally invasive treatments require appropriate non invasive real time imaging to guide the localization of the therapeutic (focal) region with respect to selected target site in the context of surrounding anatomy. This point may seem simple but it has profound implications for non-invasive treatment. This paradigm further suggests attention be paid to ensuring that the focused treatment zone be accurately and reliably aligned with whatever non-invasive imaging is used. The ideal model would be that the image plane is coincident with the therapeutic point, line or plane. Frequently, a small imaging array is placed centrally within an aperture "cut out" from a larger therapeutic array. Rosenschein [21] describes a 94 mm diameter therapeutic array into which a 7.5 MHz annular array is placed in concentric fashion. The system was used successfully for in vitro thrombolysis in bovine artery segments. Unger [22] describes (at least conceptually) a transducer design incorporating therapeutic and imaging array elements with a common front face plane. In this example, the therapeutic array is placed within a hole in the imaging array. A large central "hole" in an array aperture gives rise to a near-field blind spot and distorted sidelobe patterns—typically grating lobe related due to the poor spatial sampling implicit by virtue of the "hole" in the aperture. Until now, much work has involved fixturing an imaging array with respect to a therapeutic focused transducer/array [23-25]. An integrated imaging and therapeutic array, for example, was described by the University of Washington [26]. There is, however, no reason to believe that such an "integrated" array comprises exactly coincident "therapeutic" and imaging arrays as proposed here. The precise need for defining a required level of "integration" is a function of the particular application.

In the context of microbubble imaging, Bouakaz [27] has described a dual frequency transducer (0.9 MHz and 2.8 MHz) array using interspersed elements. The element spacing is 0.5 mm—i.e. $\lambda$ spacing at 2.8 MHz. When using an interspersed element design it becomes doubly problematic to achieve adequate spatial sampling. Further, only <50% of potential active area for each array (in isolation) is available. This loss of active area limits maximal acoustic power delivery. Forsberg [28] has also described a multifrequency array in which three linear arrays (2.5 MHz, 5 MHz and 10 MHz) were placed side-by-side with a common focal range (50 mm). This approach works well within the one fixed focal region but lacks the versatility to address other ranges.

Figures 3A, 3B, 3C:
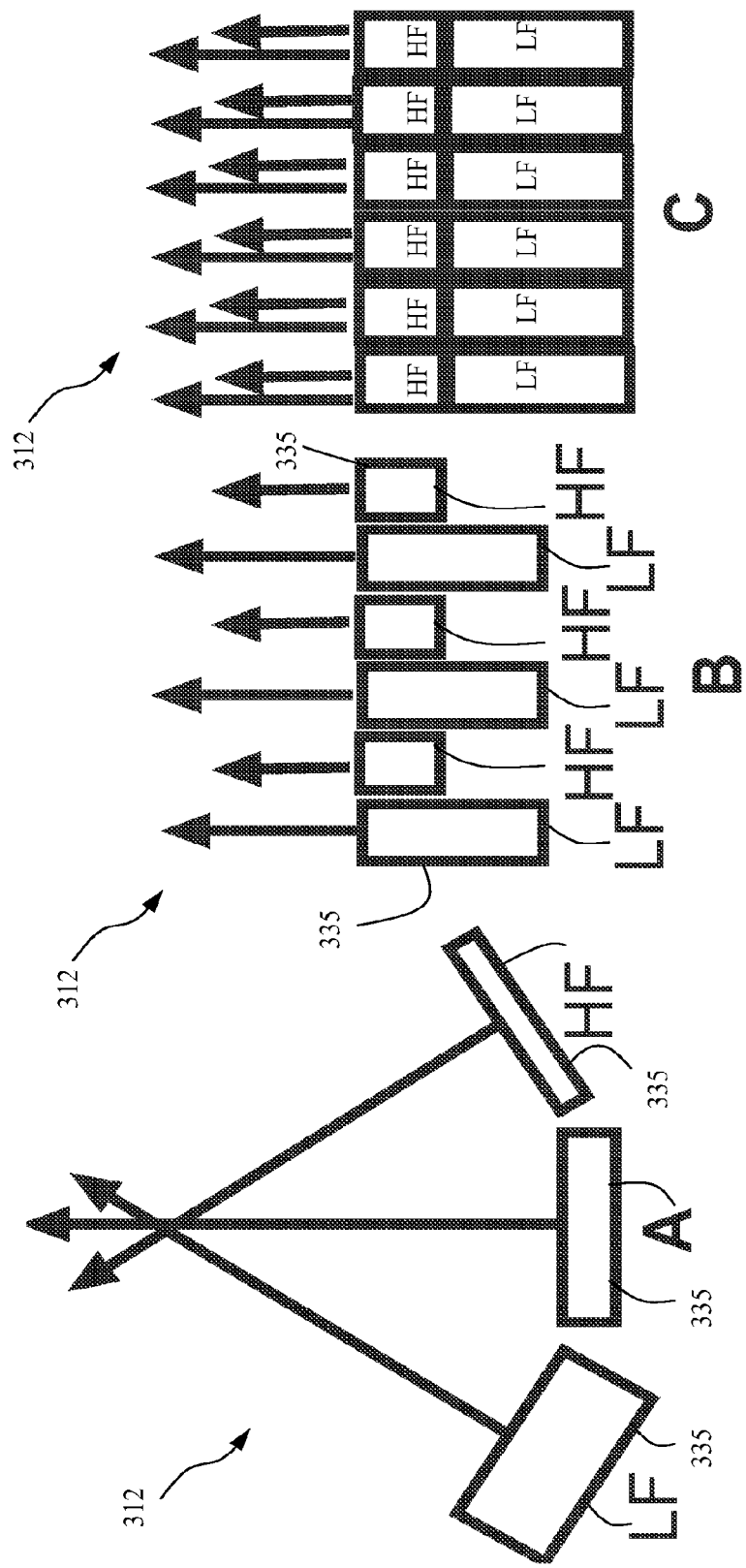
FIGS. 3(A)-(C) schematically illustrate the arrays of the Forsberg array, Bouakaz array, and present invention embodiment array, respectfully.

In an aspect of an embodiment of the present invention, there may be provided the imaging array immediately over the therapeutic array. Some advantages of an embodiment of the present invention configuration may be illustrated in FIG. 3. FIGS. 3(A)-(C) schematically illustrate the arrays of the Forsberg array (see FIG. 3(A)) having elevational view—field intersection at one pre-selected range; Bouakaz array (see FIG. 3(B)) with alternating elements of high and low frequency and having poor sampling and 50% area use per array; and an exemplary present invention embodiment of the stacked arrays (see FIG. 3(C)) having fine sampling and 100% area usage. The transducer operating frequency may be inversely related to device thickness. The High and Low frequency transducer components denoted: HF and LF, respectively. All three transducers may be implemented with various embodiments of the present invention as desired or required.

Figure 4:
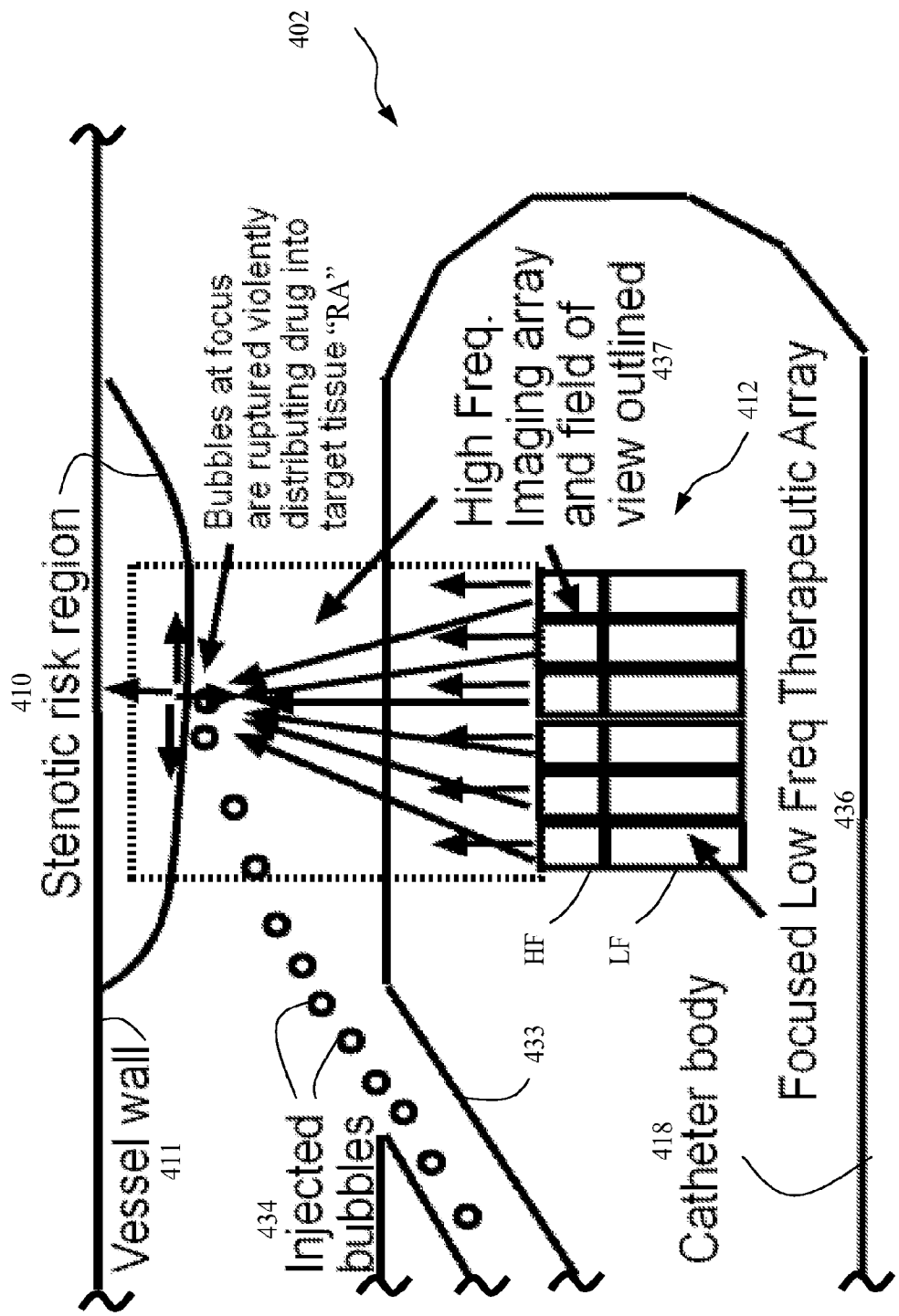
FIG. 4 schematically illustrate an embodiments (or partial embodiment) of the present invention ultrasound catheter system.

FIG. 4 schematically illustrate an embodiment (or partial embodiment) of the present invention ultrasound catheter system 402 for providing therapy (as well as diagnostic if desired or required) to a treatment site at one or more locations of a subject. The catheter system 402 may comprise a tubular member such as a catheter body 418 such or multiple catheters, needles, or lumens. The catheter(s) having a proximal region and distal region, whereby the proximal end of the ultrasound catheter is adapted or configured to be advanced to or in proximity to the subject's treatment site such as a stenotic risk region 410. It should be appreciated that any one of the catheters 418 as shown may be a plurality of catheters and any given catheter may have one or more lumens therein. The system further comprises a microbubble reservoir, port or channel 433 in hydraulic communication with the tubular member 418 and any lumens, channels, controllers or communication devices related to the catheter system. The microbubble reservoir, port or channel 433 is adapted to release microbubbles that are intended to be located into or proximal to the treatment site 410 at the desired or applicable location, such as a vessel or vessel wall 411 of the subject. The system 402 further comprises an ultrasonic energy source 412 in communication with the distal region (or other region as desired or required) of the tubular member 418 (as well as other components or subsystems of the present invention). The ultrasonic energy is adapted for, or capable of: imaging the treatment site 410, (some embodiments, for example, optionally pushing bubbles using ultrasound radiation force [29]), and rupturing the microbubbles. For instance, therapeutic array 436 for bursting the microbubbles are provided (e.g., at low frequency LF or as desired or required). Further, an imaging array 437 for imaging (e.g., at high frequency array HF or as desired or required).

Still referring to FIG. 4, the system 402 further comprise (although not shown) a control circuitry configured to send electrical activation to the ultrasonic energy source, as well as other components and subsystems of the present invention. Further, the ultrasonic energy source may provide ultrasonic radiation forces for translating the microbubbles 434 into or in the vicinity of the treatment site 410 at the desired or applicable location 411 of the subject; or alternatively the mechanical forces may be provided for translating the microbubbles into or in the vicinity of the treatment site 410, as well as a combination of both mechanical and ultrasonic forces (acoustic wave) to achieve the desired or required result.

It should be appreciated that the aforementioned catheter 418, microbubble reservoir or channel 433, ultrasound source(s) 412, and controller may be disposed entirely inside the applicable location of the subject, outside the location of the subject or a combination of inside or outside the location of the subject. The one or more locations 411 of the subject may be an organ. The organ may include hollow organs, solid organs, parenchymal tissue, stromal tissue, and/or ducts. The one or more locations 411 of the subject may be a tubular anatomical structure. The tubular anatomical structure may be a blood vessel. Further, for example, the treatment site 410 may be a vasculature treatment site comprising at least on of the following: stenosis region or any region exhibiting vascular disease. Further, for example, the treatment site 410 may be a vasculature treatment site and/or a diagnostic site.

As such, the approach illustrated in FIG. 4, provides, for instance, a catheter for delivery of drug loaded bubbles, ultrasound imaging of bubbles/tissue, and ultrasound-based bubble destruction/drug delivery.

The imaging transducer/transducer array and the therapeutic transducer/transducer array may be identical. Whereas it is sometimes necessary to optimize two transducers for two functions it is also feasible, if the transducer possesses sufficient performance versatility (e.g. high frequency bandwidth and high power capability) to use the same transducer for both imaging and therapeutic function. Ultrasound-Triggered Release of Rapamycin from Microbubbles Attenuates SMC Proliferation Over 48 hrs In Vitro.

As discussed above, the chemical and biological properties of rapamycin and why it is the benchmark reagent for preventing SMC proliferation associated with vascular injury in vivo. This established the rationale for choosing rapamycin for ultrasound-triggered microbubble carrier release. Multiple groups have shown that treatment of cultured SMCs with rapamycin reduces SMC proliferation [12, 30]. However, delivering of rapamycin via ultrasound triggered release from a microbubble carrier has not been performed.

Exemplary Design/Experiment

Ultrasound was applied to rat smooth muscle cells in conjunction with modified ultrasound microbubbles containing rapamycin in their shells. The microbubbles were prepared by co-inventor A. L. Klibanov at UVA. Microbubbles were formed by self-assembly of a lipid monolayer during the ultrasonic dispersion of decafluorobutane gas in an aqueous micellar mixture of phosphatidylcholine (2 mg/ml) and Polyethylene Glycol (PEG) stearate (2 mg/ml) with rapamycin (0.2 mg/ml) and/or a trace amount of a fluorescent dye DiI (Molecular Probes, Eugene, Oreg.), similarly to the procedure described previously [31]. Fluorescently labeled DiI microbubbles were used as a control to ensure that the microbubble vehicle alone did not cause an effect on the cells. The rapamycin drug, dissolved in 100% ethanol, was also used as a control with which to compare the effect of the rapamycin microbubbles. We assured a strong adherence of cells to the OptiCell (Biocrystal, Westerville, Ohio) flasks by plating them with fibronectin for 24 hrs prior to plating any cells. Rat SMCs were plated at a low density and allowed to grow for 48 hrs in DF10 media inside each of 12 OptiCells. Digital phase microscopy light images of the cells were taken at 5 hrs prior before treatment to establish baseline conditions. All images were taken at 4× magnification. 24 hrs after plating, the media was replaced with fresh media containing either the DiI microbubbles (vehicle control), rapamycin drug (drug control), or rapamycin microbubbles. The microbubbles (DiI or rapamycin) were added to the OptiCells at a concentration of $10\times10^6$ bubbles/ml and the rapamycin was added at a concentration of 10 ng/ml. The microbubble concentrations were chosen such that the number of microbubbles added contained an equivalent amount of rapamycin, ~10 ng/ml. We ensured that the drug had an effect even without prolonged exposure by taking half of the OptiCell flasks and giving them treatment for only two hours. After two hours the drug/bubble-containing media was replaced with fresh media. The cells in the OptiCell flasks received one of the following 6 treatments: DiI bubbles for 48 hours, rapamycin drug for 48 hours, rapamycin bubbles for 48 hours, DiI bubbles for 2 hours, rapamycin drug for 2 hours, rapamycin bubbles for 2 hours. All conditions were tested in duplicate.

Following the placement of fresh media and microbubbles into each OptiCell, ultrasound was applied to the entire area of cell growth. One at a time, each OptiCell was horizontally placed into a water bath (~37° C.). A focused 1 MHz (Panametrics, Waltham, Mass.) transducer was immersed in the water and located directly above the cells. A motion controller was used to traverse the transducer across the aperture of the OptiCell so as to evenly apply ultrasound to the entire area of cell growth. A 1 MHz, 35% BW, Gaussian pulse was applied at a Pulse Repetition Frequency (PRF) of 1 kHz, 600 kPa peak, for the entire insonation time (9 mins.). Images were taken at 4 locations within each OptiCell. These locations were marked with a dot at the 5 hr time point. Subsequent images were taken at these same locations, 24 hours, and 48 hours after treatment. The OptiCells were stored in a 37° C. incubator.

Figure 5:
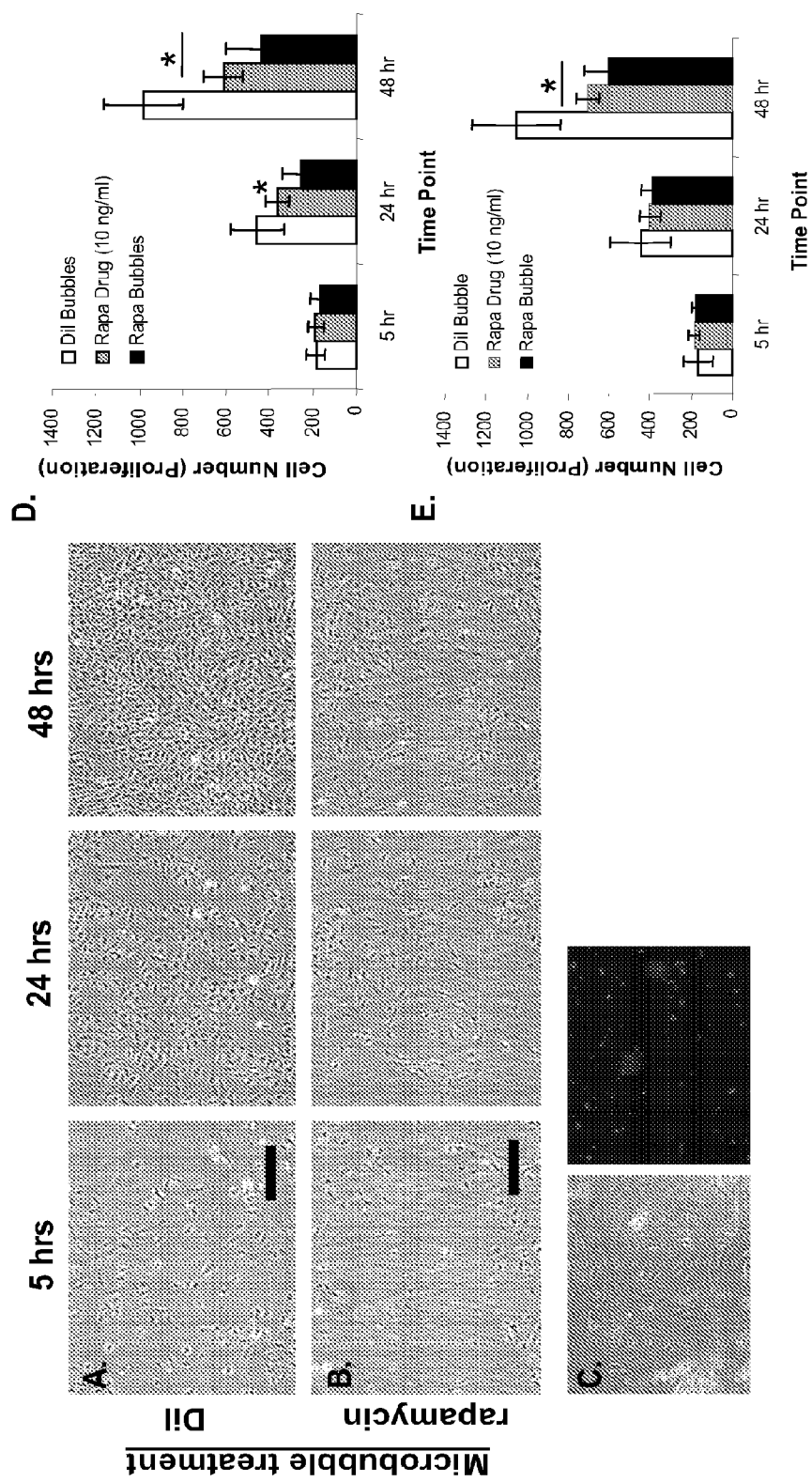
FIG. 5: illustrates the epifluorescence microscopy observations (FIG. 5A, B, C) and ultrasound backscatter imaging (FIG. 5D, E, F) of adherent microbubbles. Microcapillaries infused with buffer alone show no microbubble adhesion (A) and no ultrasound signal (dashed box illustrates microcapillary location) (D). Few adherent microbubbles are visible in flow-only microcapillaries (B), and the corresponding echo is identifiable but weak. A large number of adherent microbubbles are present in a microcapillary exposed to radiation force at 122 kPa (C), and the corresponding echo is strong. Scale bar represents 5 μm.

Results:

In FIGS. 5(A) and 5(B), we show that delivery of ~10 ng/ml of rapamycin by ultrasound-triggered release form a microbubble carrier prevented SMC proliferation, depicted as a change in cell number, compared to release of a fluorescent membrane dye, DiI (Invitrogen), from an equivalent number of microbubble carriers. Moreover, quantitative analysis in FIG. 5(D), shows that delivery of rapamycin (10 ng/ml) by ultrasound-triggered release from a microbubble carrier was not different from cells treated with free rapamycin drug (10 ng/ml) in the cell culture media. Similar results were observed in the set of 6 OptiCells which were only treated for 2 hours post ultrasound and then allowed to grow for 48 hrs (FIGS. 5(C) and 5(E)). Thus, these results show (among other things) that rapamycin and an inert cell marking dye (DiI, FIG. 5(C)) can be delivered to SMCs by ultrasound-triggered microbubble carrier release.

Figure 6:
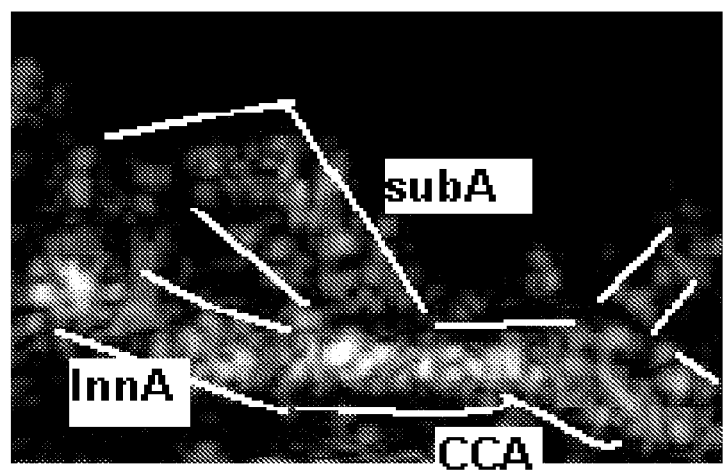
FIG. 6 illustrates a 10 MHz (e.g., Sequoia CPS) image of mouse common carotid using microbubbles with dual targeting: polymeric sialyl LewisX (psLex) and anti-mouse VCAM-1. Cho et al. "Dual-Targeted Contrast" AHA Abstract 2006. See Weller G E, Villanueva F S, Tom E M, Wagner W R. Targeted ultrasound contrast agents: in vitro assessment of endothelial dysfunction and multi-targeting to ICAM-1 and sialyl Lewisx.
Biotechnol Bioeng. 2005 Dec. 20; 92(6):780-8, of which are hereby incorporated by reference herein.
Figures 7A, 7B, 7C:
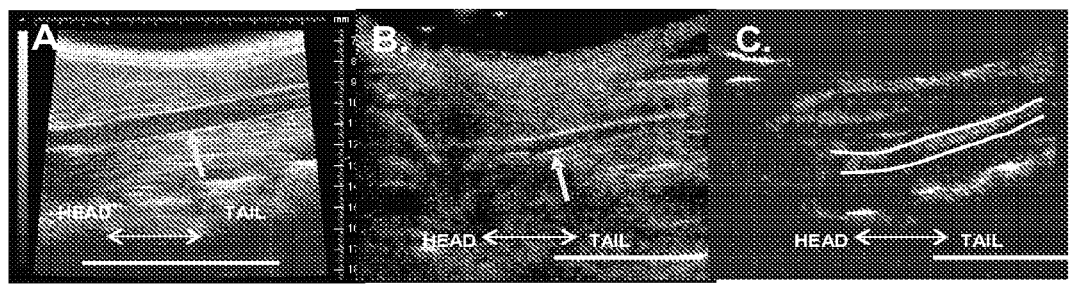
FIG. 7 illustrates: at FIG. 7(A) a B-Mode of rat carotid (40 MHz, Vevo). Yellow arrows point to the blood vessel; at FIG. 7(B) a B-mode of a rat carotid artery (12 MHz); and at FIG. 7(C) 10 MHz ultrasound imaging using bubble sensitive/specific imaging mode. White tracing denotes the carotid artery wall. White Scale bars=10 mm.

Next, non-invasive ultrasound imaging can play a critical role in the guidance of the therapeutic ultrasound that will localize the release and transcellular membrane delivery of the rapamycin drug. For instance, FIGS. 6 and 7 illustrate the current capabilities for fine-scale visualization of rodent vasculature. FIG. 6 illustrates a bubble-specific image of vessel wall-bound molecular-targeted (anti-VCAM-1) bubbles in the mouse common carotid artery (CCA) assessed using 10 MHz bubble specific ultrasound imaging (e.g., Sequoia scanner or other commercial clinical ultrasound scanner). FIG. 7(A) is a VisualSonics VEVO 770 image of a rat carotid at 40 MHz demonstrating fine spatial resolution. FIGS. 7(B) and 7(C) are B-Mode, and contrast specific, rat carotid images acquired at 12 MHz and 10 MHz, respectively (e.g., Sequoia scanner).

Transducer and Instrumentation

An exemplary transducer solution for dual function imaging therapeutics is one in which the transducer elements are sufficiently versatile that they can accomplish both tasks—high frequency (HF) imaging and low frequency (LF) bubble manipulation/breaking. This enables a design in which the imaging plane and therapeutic planes are coincident. Deficiencies in these previous designs suggest the need for a superior solution.

The solution to the dual function requirement of the transducer (HF, high resolution, low intensity imaging and LF, high power bubble fracture) is to form a transducer with two active layers: one on top of the other (for example as shown in FIG. 3(C) or FIG. 4). Each layer is resonant at a widely disparate frequency—the lower one at about 1-2 MHz and the upper one at approximately 12 MHz. Conventional design wisdom relating to stacked transducer layers would suggest that the two transducer layers would cause high undesirable interference between the resonances associated with each of the layers. Nevertheless, our experience suggests that a two layer transducer will work provided that the transducer layers are well matched between each other and to the backing material.

Figure 8:
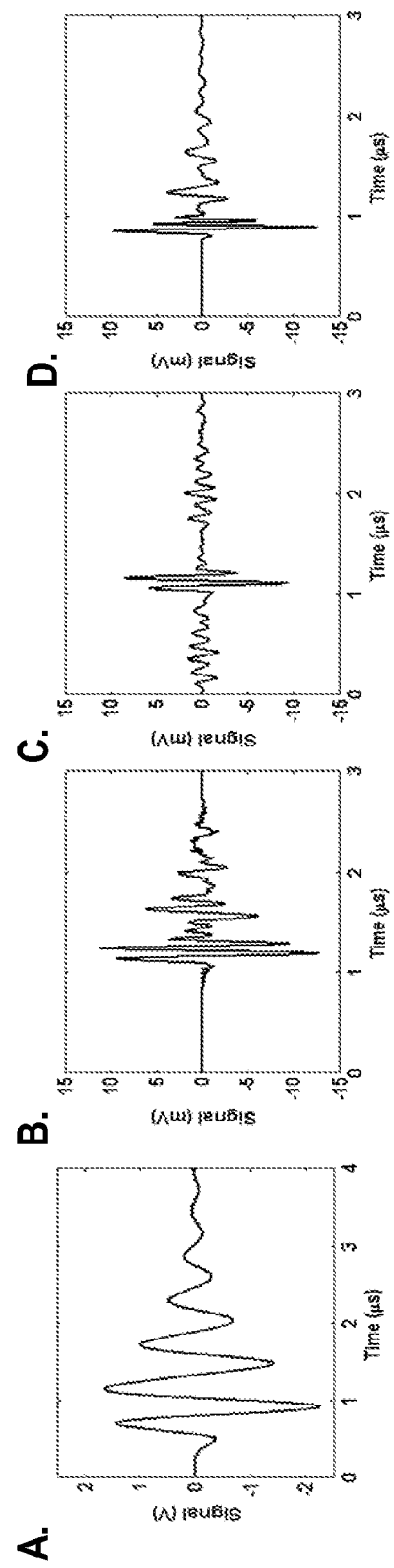
FIG. 8 illustrates prototype pulse echo responses of dual layer (multi-frequency) transducer.

In an approach, a prototype dual layer single element transducer was designed using 1:3 PZT/epoxy composite transducer layers. The acoustic impedance of each layer is approximately 15 MRayl. The backing is a dense metal (tungsten) loaded epoxy with an acoustic impedance of approximately 9 MRayl. This transducer was fabricated to our design by Vermon, Tours, France. The single element device, 1 cm in diameter and with a focal depth of 5 cm, was constructed to test the viability of the proposed dual layer approach. FIG. 8(A) illustrates the pulse-echo responses of the LF layer. The LF result exhibits a desired smooth, short duration, waveform. The high frequency layer in the current prototype exhibits a reflection artifact that we attribute to reflections between the rear of the low frequency layer and the backing block (FIG. 8(B)). In FIG. 8(C), we show that we can substantially correct this deficiency by using an inverse filter designed to force the response to be more Gaussian (in the frequency domain). Alternatively, we will redesign and optimize the dual layer transducer using better matched transducer layers to minimize/eliminate internal reflections. An early FEA result for a modified design, using a better matched backing (i.e. 15 MRayl), is shown in FIG. 8(D).

The transducer may be designed for any one of many clinical applications. It may be for transcutaneous use and comprise a conventional phased or linear array (flat or curved, or contoured anatomically or ergonomically as desired or required). It may also be designed for transesophageal, transvaginal, transuretha, transrectal or intraoperative use. Examples of each of these form factor transducers are known in the field—usually comprising similar transducer structures inside a plastic case adapted to the chosen anatomic use.

The transducer may also be formed in a catheter—as in intravascular ultrasound (IVUS). IVUS catheters are currently widely marketed in the US by Boston Scientific (Natick, Mass.) and Volcano (Rancho Cordova, Calif.). The Boston Scientific transducer typically comprises a single element that is rotated at high speed by a drive wire to form a coronal view. The transducer element in this transducer may be modified by changing its operating frequency (i.e. lowered to around 2-15 MHz) to make it suitable for breaking bubbles. The Volcano transducer is generally a circumferential phased array. Again, the frequency of the array design may be modified (i.e. lowered to around 2-around 15 MHz) to make it suitable for breaking bubbles. It is possible to potentially use either a dual layer design—as described herein—or potentially use a modified design where a compromise between high frequency imaging and low frequency bubble breaking is selected—e.g., instead of attempting to operate imaging at about 25 MHz and breaking at about 2 MHz, a single wideband design at about 15 MHz is capable of about 8 MHz breaking and 20 MHz imaging. High bandwidth transducer design, such as by using multiple matching layers, for example, as known to those skilled in the art. As shown in FIGS. 4 and 12, for example, the catheter transducer may also include a continuous hollow port down which drug coated contrast is flushed during use. In this way, a stream of active contrast is emitted into the field of view of the transducer as shown schematically. (In clinical use, the blood flow in the coronaries is in the "right" direction—i.e. blood flow is moving in the distal orientation).

Notice also that other formats of drug media delivery are possible. For example: free dissolved (e.g. alcohol) rapamycin (or other drug) may be transferred side by side with plain contrast microbubbles down the hollow port. As indicated in Price's 1998 Circulation paper ("Delivery of colloidal particles and red blood cells to tissue through microvessel ruptures created by targeted microbubble destruction with ultrasound" Vol. 98, No 13, pp 1264-1267), local bubble breakage enables delivery of colloidal material (including potential drug in dissolved or undissolved form) across microcirculatory vessel walls. Bubble could be injected intravenously and dissolved rapamycin may be injected via the catheter port.

Normally lipid based bubbles are used. Other shell materials may be used—such as albumen-based or polymer-based shelled bubbles. Bubbles with these shell materials are known in the field.

Instrumentation

Among various options available, the SonixRP (Ultrasonix, Richmond, BC, Canada) is a versatile platform to use as the base instrumentation for implementing the invention. Of course, other scanner platforms may be procured or designed/built as is well known to those in the field. The RP, and its research capabilities (including high level software/hardware architecture), are described in detail in a recent publication [32] [32].

It should be appreciated a number of marketed technology systems and components may be implemented with the present invention such as by, but not limited to, the following: the medical ultrasound companies include: Philips, Siemens, General Electric—also VisualSonics etc. However, it may be noted that these are not catheter based companies. BostonScientific and Volcano are the primary IVUS companies.

In vitro Radiation Force Enhanced Molecular Targeted Ultrasound

A problem encountered when using intravascular injected targeted contrast agent is that, except in very small vessels, only a very small fraction of the injected material will be sufficient close (<1 μm) to have even a remote chance to form the intended molecular bond between ligand and receptor. In vitro studies of targeted microbubble adhesion on substrates of P-selectin have reported that only a small percentage of the perfused microbubbles were specifically retained under physiological flow conditions [e.g., Klibanov [33]]. Although detection of single microbubbles is possible [34], low efficiency of microbubble targeting requires a larger administered dose of microbubbles than would otherwise be required. Microbubbles exhibit rheological behavior similar to that of erythrocytes [35] and tend to migrate towards the center of the blood vessel. As most endothelial proteins extend only nanometers [36] from the endothelium, it is unlikely that many of the microbubbles flowing through the targeted vasculature come into contact with the intended molecular target. Microbubble attachment efficiency can be increased by moving circulating microbubbles into contact with the vessel wall, thus increasing the frequency of microbubble: target adhesive events. Dayton [37] and others [38] previously hypothesized that microbubble adhesion to the vascular endothelium may be enhanced by using ultrasound radiation forces to propel freely flowing microbubbles towards the vessel wall. Adhesion of microbubbles [39] and acoustically active liposomes [40] under applied acoustic pressure in an avidin: biotin model system has been examined, and adhesion of targeted microbubbles to cultured endothelial cells has been reported [39].

Acoustic radiation traveling through a continuous media produces a pressure gradient, which is experienced as a directional force by compressible bubbles in the acoustic field. Two components of this radiation force have been described: a primary force, which is directed away from the source, and a secondary force, which is typically attractive between ultrasound contrast microbubbles [41]. The behavior of single, free-stream microbubbles exposed to acoustic radiation has previously been examined rigorously [37, 41, 42]. Derivations of the magnitude of both primary and secondary forces in the linear range were presented by Dayton [37], assuming a low duty factor, a constant magnitude of pressure in each applied pulse, and a unidirectional pressure gradient. The primary radiation force is proportional to the negative time-averaged product of the microbubble volume and the spatial pressure gradient. For a microbubble driven at resonant frequency, assuming small-amplitude oscillations, the magnitude of the primary radiation force is defined by $$F_1 = \frac{2\pi P_a^2 R}{\delta \omega_0 \rho c} \left[ \frac{D}{T} \right] \quad (1)$$

where $P_a$ is the peak applied acoustic pressure, R is the microbubble resting radius, δ is the total damping coefficient, ρ is the medium density, c is the velocity of sound in the bulk aqueous phase, and ω0 is the microbubble resonant frequency. This term is scaled by D/T for a pulsed field, where D is the pulse duration and 1/T is the pulse repetition frequency (PRF).

Figure 9:
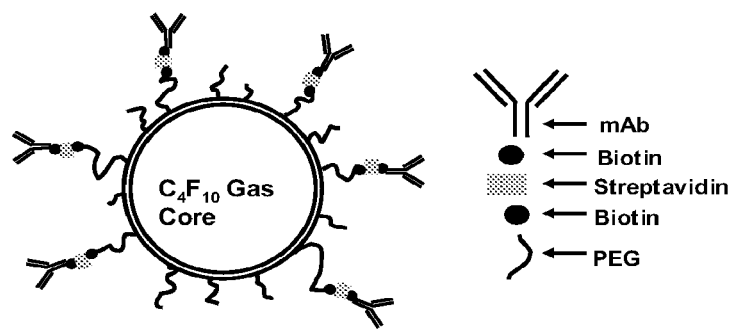
FIG. 9 illustrates a diagram of targeted ultrasound contrast microbubble. The gas core is encapsulated by a lipid monolayer shell, which is coated with a PEG brush. The targeting ligand, here an anti-P-selectin monoclonal antibody, is secured to the distal tips of the polymers via a biotin-streptavidin link. Figure is not to scale.

Targeting these microbubbles to P-selectin was achieved by conjugating the anti-P-selectin monoclonal antibody (mAb) Rb.40.34 [43] to the distal tips of PEG chains via a streptavidin link, as shown in FIG. 9. The preparation of the targeted microbubbles used in this experiment has been described in depth elsewhere [31, 44]. Trace amount (<1% of total lipid mass) of DiI lipid dye (Molecular Probes, Eugene, Oreg.) was used as a fluorescence probe for epi-illumination microscopy. Microbubbles were conjugated to the targeting ligand the day of the experiment, and were stored on ice in C4F10-saturated Dulbecco's Phosphate Buffered Saline Solution (DPBS) (Invitrogen, Carlsbad, Calif.). Microbubble size distribution and concentration was determined with a Coulter counter (Beckman-Coulter, Miami, Fla.).

Figure 10:
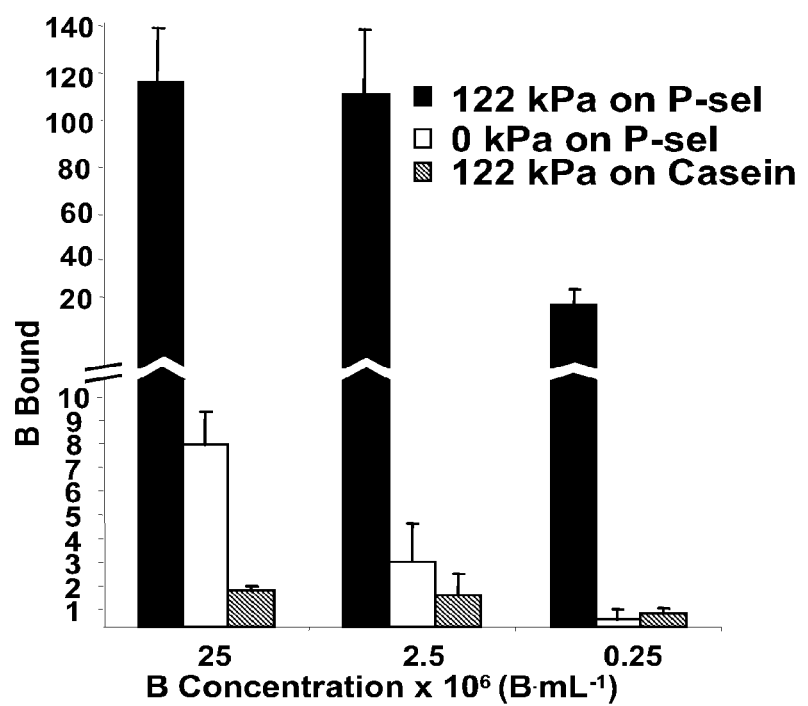
FIG. 10 illustrates a microbubble adhesion at wall shear rate of 355 s-1 on P-selectin after insonation at 122 kPa (122 kPa on P-sel; n=4), adhesion on P-selectin after flow alone (0 kPa on P-sel; n=3), and adhesion on casein after insonation at 122 kPa (122 kPa on Casein—i.e. control); n=3). Mean number of adherent microbubbles per 10 optical fields+standard deviation. Insonated capillaries exhibited significantly greater adhesion (p<0.05) than that of the flow only or insonated capillaries at each condition examined. The break in vertical scale may be noted.

A 2.25 MHz, 0.5" diameter, 0.8" focal depth ultrasound transducer (Panametrics V306, Waltham, Mass.) was used in this study. At a Pulse Repetition Frequency (PRF) of 10 kHz, 40 sinusoidal cycles at a frequency of 2.0 MHz were applied. Microbubbles were insonated at acoustic pressures between 24.5 and 170 kPa. Upon cessation of insonation, 10 optical fields along a P-selectin coated microcapillary within the width of the applied ultrasound beam were observed and recorded. Alternatively, some flow chambers were exposed to 2 minutes of flow alone, without insonation, in order to assess microbubble binding in the absence of applied radiation force. The number of adherent microbubbles in each of 10 fields of view following insonation was determined off-line. Microbubbles aggregates projecting normal to the optical plane (downward into the flow stream) were counted as a single bubble. Microbubble aggregation was assessed by counting the number of contiguous microbubbles adherent in the optical plane. Each flow chamber was used for a single experiment. Statistical significance was tested with a Student's t-test. We observed negligible binding of targeted microbubbles to casein-coated (i.e. control) microcapillaries both with and without the application of radiation force, see FIG. 10. We observed a statistically significant (p<0.05) increase in specific microbubble adhesion to P-selectin due to applied radiation forces at each of the microbubble concentrations examined. Applied radiation force increased targeted microbubble adhesion to P-selectin coated microcapillaries 16-fold at $75 \times 10^6$ B ml$^{-1}$ and over 60-fold at $0.25 \times 10^6$ B ml$^{-1}$ (or other sizes, volumes and ranges as required or desired).

Figure 11:
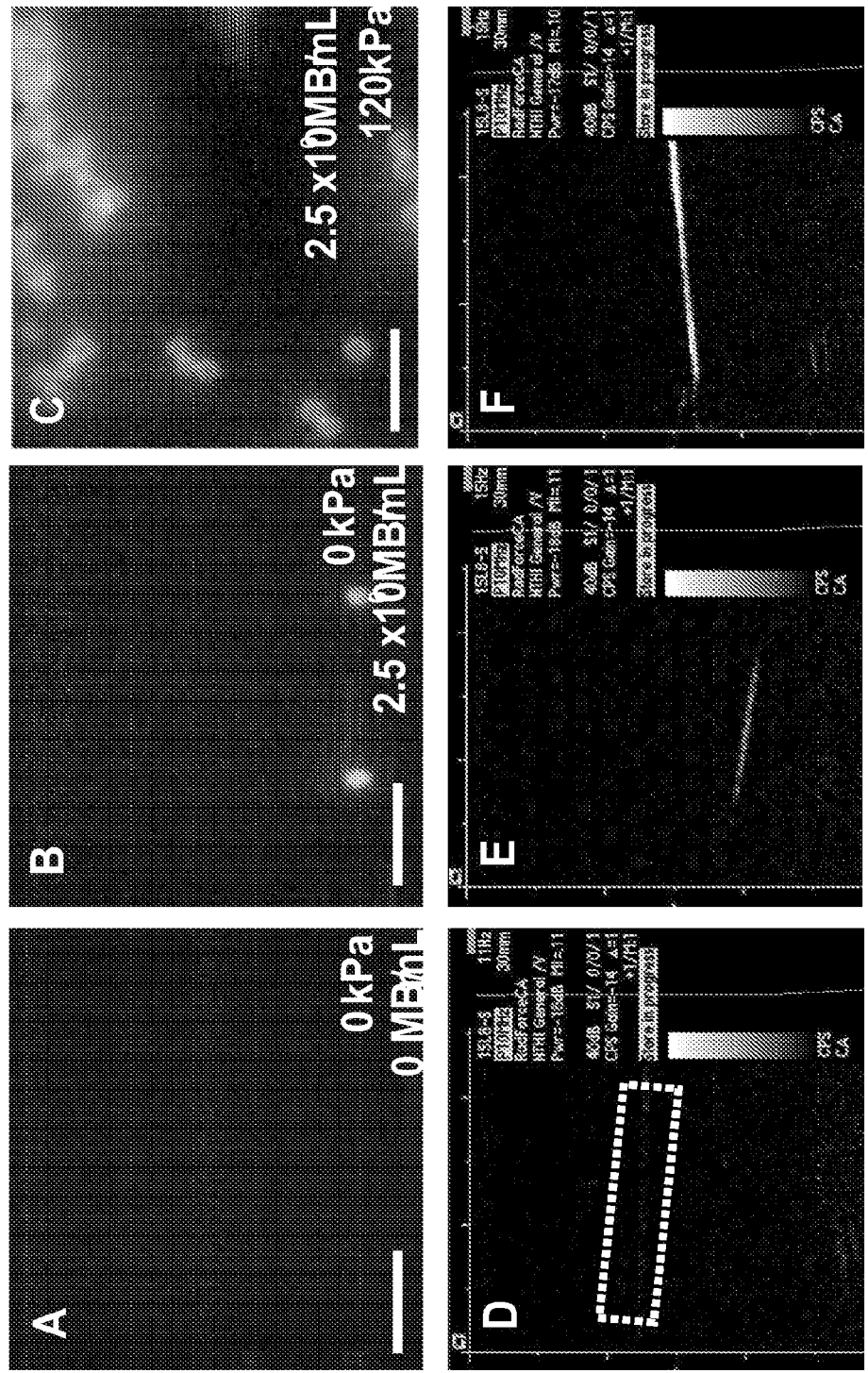
FIG. 11 illustrates an epifluorescence microscopy observations (FIGS. 11(A), 11(B), 11(C)) and ultrasound backscatter imaging (FIGS. 8(D), 8(E), 8(F)) of adherent microbubbles. Microcapillaries infused with buffer alone show no microbubble adhesion (A) and no ultrasound signal (dashed box illustrates microcapillary location) (FIG. 11 (D)). Few adherent microbubbles are visible in flow-only microcapillaries (FIG. 11 (B)), and the corresponding echo is identifiable but weak. A large number of adherent microbubbles are present in a microcapillary exposed to radiation force at 122 kPa (FIG. 11 (C)), and the corresponding echo is strong. Scale bar represents 5 μm.

Imaging of adherent microbubbles in flow chambers was also performed using 14 MHz ultrasound imaging (e.g., on a Siemens Sequoia or similar clinical scanner). Microbubbles were infused into the flow chamber as described above and exposed to 1 minute of flow alone at the indicated shear rate, followed by one minute of insonation at 122 kPa or 1 additional minute of flow only. It has also been determined that microbubbles attached to the target substrate by acoustic radiation force remain viable for ultrasound imaging. We observed no adherent microbubbles and received no ultrasound signal in microcapillaries infused with buffer alone (FIG. 11(A), FIG. 11(D)). A contrast signal is visible in FIG. 11(E), which shows an ultrasound image of a microcapillary infused with 2.5×106 B/ml for 2 minutes in the absence of acoustic pressure then flushed with buffer. A representative fluorescence microscopy field of view in this capillary is presented in FIG. 11(C). FIG. 11(B). FIG. 11(C) shows a representative optical field of view from a microcapillary infused with $2.5 \times 10^6$ bubbles/ml exposed to 1 minute of flow only, 1 minute of insonation at 122 kPa and then saline flushed, in which extensive microbubble accumulation is evident. The corresponding echo shown in FIG. 11(F) is very strong. This suggests that the microbubbles targeted by means of radiation force at an acoustic pressure of 122 kPa remain intact and echogenic.

In summary, we have demonstrated some of the key components of some of the embodiments of the present invention method and system including, but not limited thereto, the following:

1. Rapamycin loaded microbubbles+ultrasound have a demonstrated, selective, anti-proliferative effect on rat SMCs.

2. VCAM-1, as well as other cell surface antigens including but not limited to PECAM, is upregulated in proliferating SMCs in the rat and other animal models of stenosis and human restenosis.

3. Fine resolution ultrasound imaging can visualize vasculature anatomy and achieve high sensitivity/high specificity bubble imaging.

4. Dual frequency transducers for: a) high frequency imaging, and b) low frequency radiation force/bubble fracture.

5. Radiation force can be used to improve bubble molecular VCAM-1 targeting attachment efficiency.

Related Exemplary Methods (and Related Systems)

Single Element Transducer (Typically Non Imaging Capable).

Our preliminary data provided promising early results using a simple, axisymmetrically focused, single element transducer. What is required is a dual function (low frequency bubble "busting" plus high frequency imaging) transducer and associated instrumentation.

Transducer Array (Typically Imaging Capable).

An exemplary design may comprise 1:3 composite piezoceramic—epoxy active layers stacked one over the other. (A "1:3" composite comprises piezoelectric ceramic posts embedded in a polymer matrix—i.e. the two components are electrically and mechanically in "parallel". The 1:3 configuration is the dominant composite configuration and is in widespread commercial use). The composite material possesses approximate 50% ceramic volume fraction and possesses an acoustic impedance of approximately 15 MRayl. A dense, tungsten particle filled, backing block is used. A thin matching layer, approximately quarter wavelength matched for 12 MHz operation, is used over the top. A conventional filled silicone rubber lens will be used to obtain an elevation focus. The elevational focal depth is approximately 15 mm. Specifically, we use approximately 12 MHz B-Mode imaging resulting in <200 µm lateral resolution and axial resolution. At this frequency, $\lambda$ is 125 µm. Consequently, for practical f#'s, (i.e. 1-2) a 200 µm resolution is feasible. An array system provides more than sufficient scanning frame rate (>100 frames/s for selected small fields of view—e.g. 15 mm×15 mm). Focused ultrasound delivery is delivered at 1-2 MHz. We are able to control the region over which a therapeutic effect is obtained to approximately $3\lambda$—i.e. approximately a 2 mm spot size.

High Resolution, High Sensitivity, High Specificity, Bubble Imaging.

An objective is to provide anatomic B-Mode imaging capability, bubble specific imaging and application of bubble fracture pulses under user control. The anatomic B-Mode imaging are accomplished using standard B-Mode image formation techniques—i.e. optimized aperture apodization, fixed focus transmit, dynamic receive focusing, signal detection and scan conversion. Bubble specific imaging will be provided by using "Pulse Inversion" (PI)[45]— i.e. 1, −1 transmit polarity/amplitude; followed by "1"+"−1" processing to eliminate the linear component). If necessary other bubble specific techniques such as amplitude scaling (i.e. 1, 2 transmit polarity/amplitude; followed by (2×"1")—"2" processing [46]) and the combination of PI and amplitude scaling (e.g. −1, 2, −1 transmit polarity/amplitude; followed by "−1"+"2"+"−1" processing [47]).

Low Frequency, Bubble Pushing and Bubble Destruction.

These modes use the low frequency elements of the array. The design of an embodiment for the transducer comprises less than a total of 128 elements (96, 12 MHz elements and 24, 2 MHz elements). In this way, by simply reprogramming the selected transducer apertures from the available 128 transducer connector channels, we can switch between imaging and therapeutic modes of operation.

Design Rapamycin Microbubble Carrier System Capable of Ultrasound-Triggered Release Bubble Making and Rapamycin Incorporation.

Microbubbles are prepared by self-assembly of a lipid monolayer during the ultrasonic dispersion of decafluorobutane gas in the aqueous micellar mixture of phosphatidylcholine and PEG stearate (2 mg/ml) with rapamycin (0.2 mg/ml) and/or a trace amount of a fluorescent dye DiI (Molecular Probes, Eugene, Oreg.), similarly to the procedure described earlier [48]. In some instances, membrane thickening is achieved by addition of glycerol trioleate (thicker microbubble shell will harbor increased amounts of rapamycin) [49]. Free lipid, dye and rapamycin, not incorporated in the bubble shell is removed by sequential (3×) centrifugal flotation (100×g, 5 min), with the recycling of the first wash to save reagents.

Rapamycin Quantitation.

Robust and sensitive high performance liquid chromatography (HPLC) procedures are described in the literature for clinical assays. We have HPLC available in our laboratory and will implement such a procedure [50]. Briefly, the sample being tested (microbubbles or media) is lyophilized and redissolved in chlorobutanol, centrifuged to remove sediment; samples placed in the autosampler vials and HPLC performed with UV detection against a calibration curve with a known amount of rapamycin.

Rapamycin Release by Ultrasound: In Vitro Functional Bubble Destruction Testing.

An aqueous saline dispersion of rapamycin-containing microbubbles ($10^6$-$10^7$/ml particle concentration) will be placed in an OptiCell (USA Scientific, Ocala, Fla.) in 10 ml volume. We will destroy bubbles by ultrasound in the conditions described for the cell culture study, remove the microbubble particles from OptiCell and subject them to centrifugal flotation to prove that residual microbubbles (if present) will be removed from the samples. We will then perform rapamycin quantitation in the bubble-free infranatant by HPLC technique as described above.

Attachment of Anti-VCAM-1 Antibody to Microbubbles.

Coupling of anti-VCAM-1 antibody to microbubble surface is performed by streptavidin coupling technique as described [44]. Briefly, during the preparation of microbubbles, 2 mol % of biotin-PEG3400-phosphatidylethanolamine is added to the lipid mixture. A streptavidin bridge technique is applied for biotinylated anti-VCAM-1 antibody coupling to the microbubble surface as described earlier for other antibodies [33, 51]. Biotinylation of antibody molecule is performed with biotin N-hydroxysuccinimide ester reagent at pH 7.5 in DPBS buffer. The degree of antibody biotinylation is tested using the HABA assay as described previously [e.g., Klibanov [33]]. By the adjustment of the antibody-to-biotin-NHS, an incubation ratio coupling of ~1 biotin per antibody will be achieved. The ELISA test on VCAM-1 antigen is used to confirm that biotinylation does not inactivate the antibody. Streptavidin-bubbles ($10^9$/ml) are incubated with biotinylated antibody on ice for 30 min; free antibody are removed from the bubbles by triple centrifugal flotation wash with degassed DPBS buffer in a bucket-rotor centrifuge (100×g, 5 min). After repeated flotations, the mean size of antibody-coated bubbles is normally ~2.5 um, with >99% of the particles less than 8 um (particle size and concentration are evaluated with a Coulter Multisizer IIe instrument (Beckman Coulter, Miami, Fla.). The amount of attached antibody per bubble is tested by fluorescence spectroscopy labeling as described earlier; typically, ~$10^5$ antibody molecules per microbubble are attached by this technique [51].

Figure 12A:
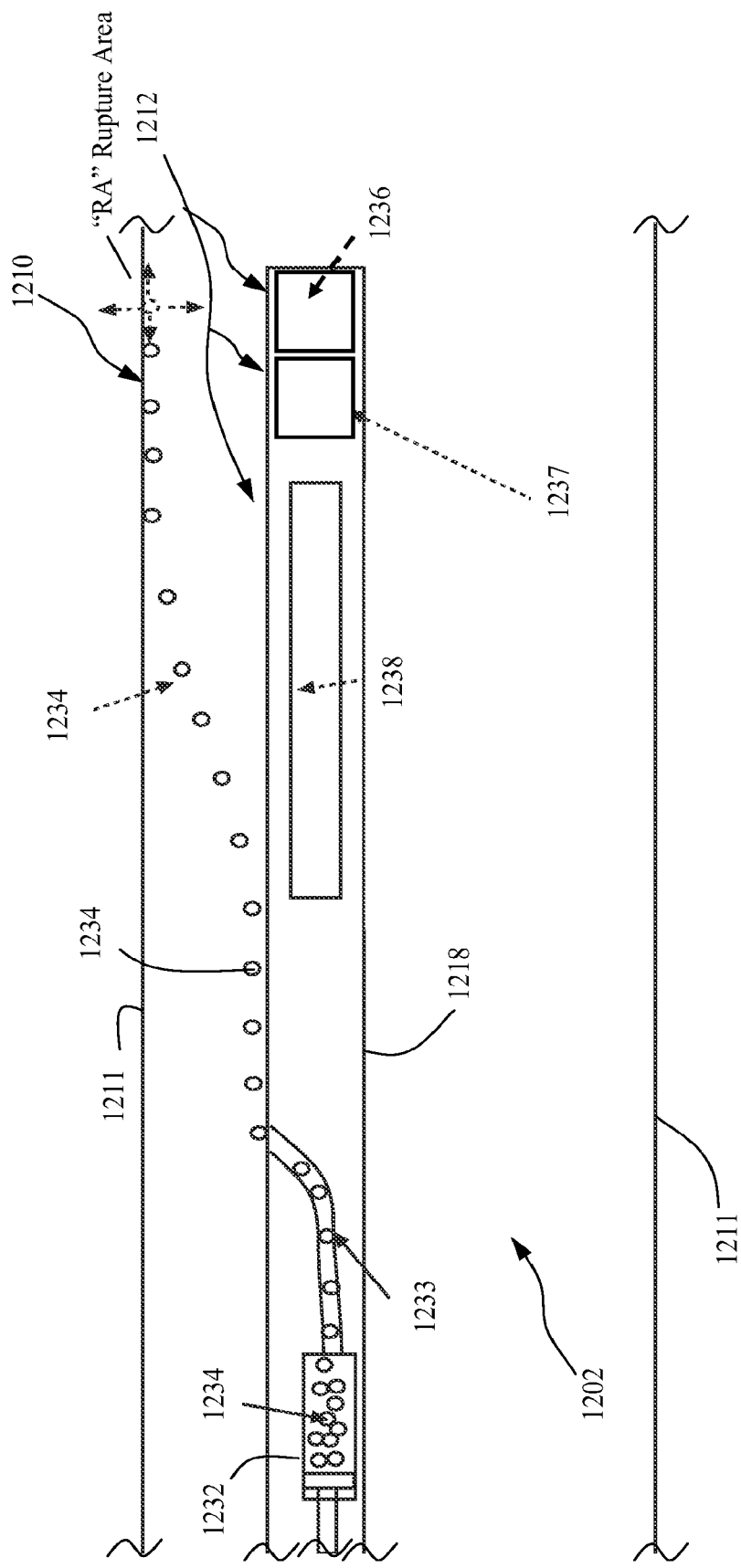
FIGS. 12(A)-(B) schematically illustrate various embodiment (or partial embodiments thereof) of the present invention ultrasound catheter system.

FIG. 12(A) schematically illustrate an embodiments (or partial embodiment) of the present invention ultrasound catheter system 1202 for providing therapy (as well as diagnostic if desired or required) to a treatment site at one or more locations of a subject. The catheter system 1202 may comprise a tubular member 1218 or other conduit or chamber, such or multiple catheters, needles, or lumens. The catheter(s) having a proximal region and distal region, whereby the proximal end of the ultrasound catheter is adapted or configured to be advanced to or in proximity to the subject's treatment site or region 1210. It should be appreciated that any one of the tubular member 1218 as shown may be a plurality of tubular or conduit members and any given catheter or the like may have one or more lumens therein. The system further comprises a microbubble reservoir 1232 in hydraulic communication with the port or channel 1233 and in hydraulic communication with the tubular member 1218 and any lumens, channels, controllers or communication devices related to the catheter system. The microbubble reservoir 1232 and port or channel 1233 is adapted to release microbubbles that are intended to be located into or proximal to the treatment site 1210 at the desired or applicable location 1211 of the subject 1211, such a vessel, organ, anatomical structure, anatomical tubular structure, or duct, etc. The system 1202 further comprises an ultrasonic energy source(s) 1212 in communication with the distal region (or other region as desired or required) of the tubular member 1218 (as well as other components or subsystems or components of the present invention). The ultrasonic energy is adapted for or capable of: imaging the treatment site 1210, and rupturing the microbubbles. For instance, therapeutic array 1236 (comprising a predetermined ultrasound system design as desired or required) for bursting the microbubbles are provided (e.g., at low frequency LF or as desired or required). Further, an imaging array 1237 (comprising a predetermined ultrasound system design as desired or required) is provided for imaging (e.g., at high frequency array HF or as desired or required). Further yet, the ultrasonic energy source 1238 (comprising a predetermined ultrasound system design as desired or required) may provide ultrasonic radiation forces for translating or transporting the microbubbles 1234 (e.g., at low frequency LF or high frequency HF, or combination thereof, or as desired or required) into or in the vicinity of the treatment site 1210 or region at the desired or applicable location 1211 of the subject.

Still referring to FIG. 12(A), the system 1202 further comprise (although not shown) a control circuitry configured to send electrical activation to the ultrasonic energy source, as well as other components and subsystems of the present invention. Further, regarding the translation or transportation of the microbubbles or applicable medium, mechanical forces may be provided may be provided in place of the ultrasound forces (acoustic wave) or in combination with the ultrasound for translating the microbubbles into or in the vicinity of the treatment site 1210 to achieve the desired or required result.

It should be appreciated that the aforementioned catheter 1218, microbubble reservoir 1232, microbubble port or channel 1233, ultrasound source(s) 1212, and controller may be disposed entirely inside the applicable location of the subject 1211, outside the location of the subject or a combination of inside or outside the location of the subject. The one or more locations 1211 of the subject may be an organ. The organ may include hollow organs, solid organs, parenchymal tissue, stromal tissue, and/or ducts. The one or more locations 1211 of the subject may be a tubular anatomical structure. The tubular anatomical structure may be a blood vessel. Further, for example, the treatment site 1210 may be a vasculature treatment site comprising at least on of the following: stenosis region or any region exhibiting vascular disease. Further, for example, the treatment site 1210 may be a vasculature treatment site and/or a diagnostic site.

Figure 12B:
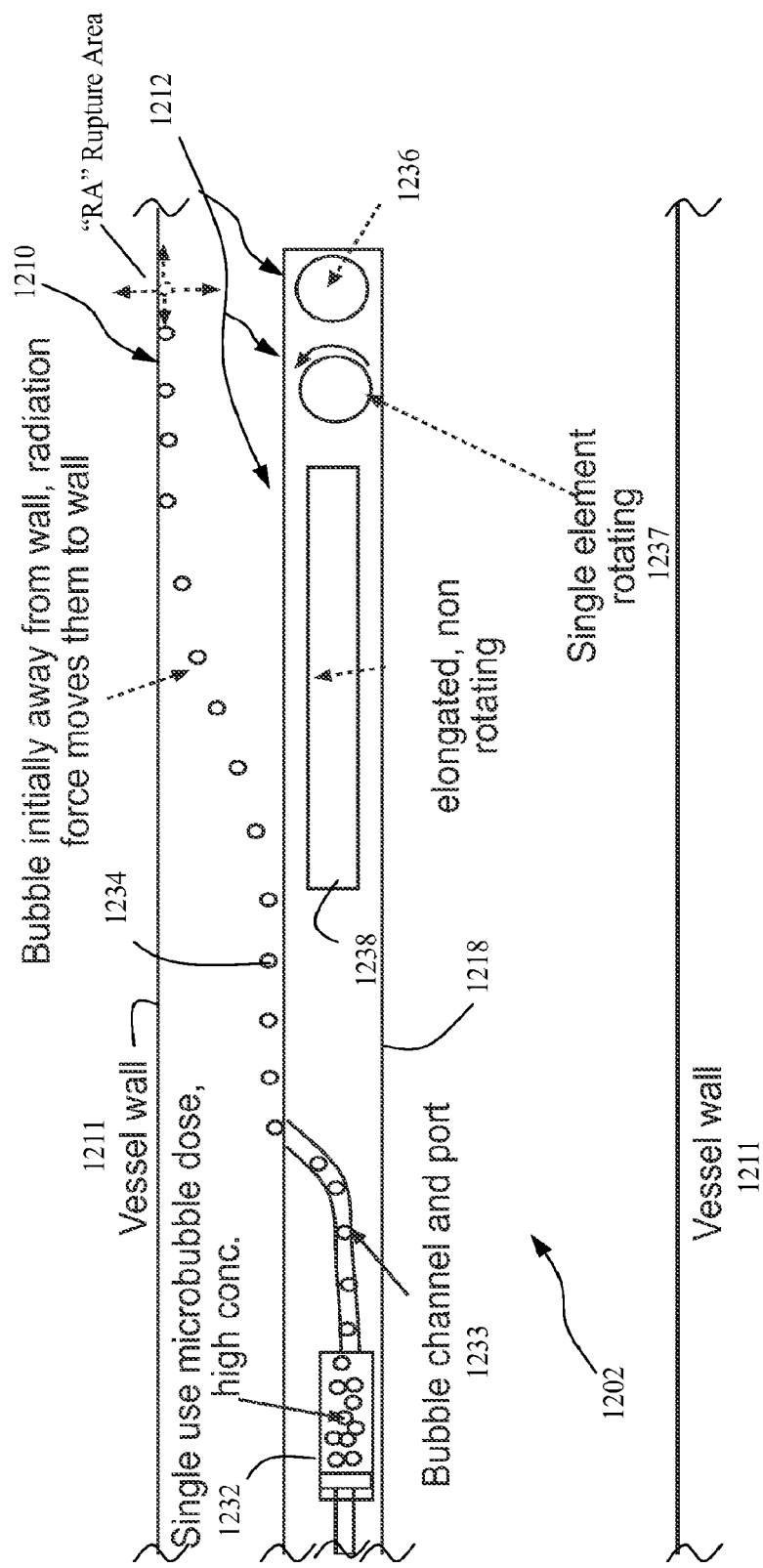

FIG. 12(B) schematically illustrate an embodiments (or partial embodiment) of the present invention ultrasound catheter system 1202 for providing therapy (as well as diagnostic if desired or required) to a treatment site at one or more locations of a subject. The catheter system 1202 may comprise a tubular member such as a catheter body 1218 such or multiple catheters, needles, conduits, housings, or lumens. The catheter(s) having a proximal region and distal region, whereby the proximal end of the ultrasound catheter is adapted or configured to be advanced to or in proximity to the subject's treatment site or region 1210. It should be appreciated that any one of the catheters 1218 as shown may be a plurality of catheters and any given catheter may have one or more lumens therein. The system further comprises a microbubble reservoir 1232 in hydraulic communication with the port or channel 1233 and in hydraulic communication with the tubular member 1218 and any lumens, channels, controllers or communication devices related to the catheter system. The microbubble reservoir 1232 may be single use microbubble dose and high concentration. Moreover, the reservoir 1232 may comprise multiple uses and have a variety of concentrations as desired or required. The microbubble reservoir 1232 and/or port or channel may be a capillary size or larger, or the microscale or smaller such as a microchip, lab-on-a-chip, or in-situ design. The microbubble reservoir 1232 and port or channel 1233 is adapted to release microbubbles that are intended to be located into or proximal to the treatment site 1210 at the desired or applicable location, such as a vessel or vessel wall 1211 of the subject. The system 1202 further comprises an ultrasonic energy source 1212 in communication with the distal region (or other region as desired or required) of the tubular member 1218 (as well as other components or subsystems of the present invention). The ultrasonic energy is adapted for or capable of: imaging the treatment site 1210, and rupturing the microbubbles. For instance, therapeutic array 1236 for bursting the microbubbles are provided (e.g., at low frequency LF or as desired or required). The therapeutic array 1236 comprises a bubble rupture transducer that may be a rotating type; or may be a non-rotating type and be aligned with the radiation force transducer 1238 (or any combination thereof). Further, an imaging array 1237 is provided for imaging (e.g., at high frequency array HF or as desired or required). The imaging array 1237 may be rotating or non-rotating and may be a single element or multiple element (or any combination thereof). Further yet, the ultrasonic energy source 1238 may provide ultrasonic radiation forces for translating or transporting the microbubbles 1234 (e.g., at low frequency LF or high frequency HF, or combination thereof, or as desired or required) into or in the vicinity of the treatment site 1210 at the desired or applicable location 1211 of the subject. The radiation force transducer 1238 may be elongated and non-rotating. Alternatively, the shape may also vary and it may rotate as well. Alternatively, rather than a radiation force transducer, a means for transporting or translating may be implemented, such as mechanically or electrically. For instance, but not limited thereto, ejecting the bubbles with sufficient peripheral oriented velocity so as to translate quickly to the vessel wall.

Still referring to FIGS. 12(A)-(B), the system 1202 further comprise (although not shown) a control circuitry configured to send electrical activation to the ultrasonic energy source, as well as other components and subsystems of the present invention. Further, regarding the translation or transportation of the microbubbles or applicable medium, mechanical forces may be provided in place of the ultrasound forces (acoustic wave) or in combination with the ultrasound for translating the microbubbles into or in the vicinity of the treatment site 1210 to achieve the desired or required result.

It should be appreciated that the aforementioned catheter 1218, microbubble reservoir 1232, microbubble port or channel 1233, ultrasound source(s) 1212, and controller may be disposed entirely inside the applicable location of the subject, outside the location of the subject or a combination of inside or outside the location of the subject. The one or more locations 1211 of the subject may be an organ. The organ may include hollow organs, solid organs, parenchymal tissue, stromal tissue, and/or ducts. The one or more locations 1211 of the subject may be a tubular anatomical structure. The tubular anatomical structure may be a blood vessel. Further, for example, the treatment site 1210 may be a vasculature treatment site comprising at least on of the following: stenosis region or any region exhibiting vascular disease. Further, for example, the treatment site 1210 may be a vasculature treatment site and/or a diagnostic site.

Still referring to FIGS. 12(A)-(B), for example (as well as other embodiments discussed herein), the system 1202 may comprise, but not limited to the following:
   Imaging transducer may be scanned single element or array;
   Orientation of scanning transducer/array may be annular format per conventional;
   IVUS or may be longitudinal (or other) format;
   Longitudinal format is like shown here for the radiation force transducer and may be similar to the Siemens AcuNav intracardiac catheter transducer array;
   Radiation force transducer may be a single element, focused element;
   It might be an annular array for multiple focal option;
   Frequency of each transducer/array may be different;
   Radiation force transducer may be high frequency;
   Imaging radiation may be high frequency;
   Rupture radiation may be low frequency;
   Rupture and imaging could be coincident—one over the other;
   Bubbles are conceptually injected via a port;
   Bubbles may be injected freely via the same access catheter (i.e. ~2 mm tube or as desired);
   Bubbles may be saved in a single use highly concentrated from near the catheter tip. This would allow us to use a smaller number of bubbles. Keeping the bubbles in high concentration (i.e. low rate of outward diffusion) allows them to be time stable);
   Bubbles may be monodisperse (all same size), but not necessarily;
   In principle, bubble dispersions can be sorted.

Figure 13:
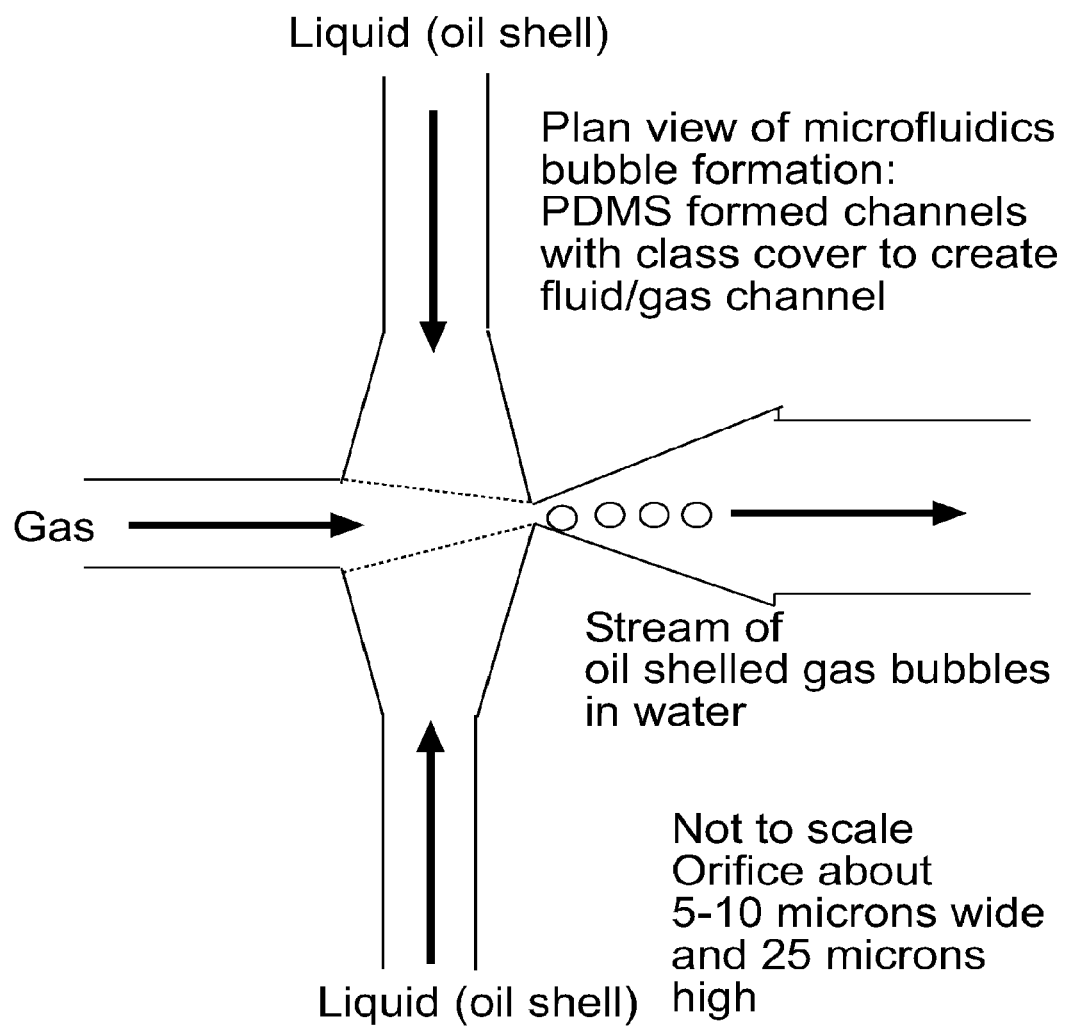
FIG. 13 provides a plan schematic view of the microfluidic flow-focusing device or in-situ device.

FIG. 13 illustrates a schematic plan view of the "On-chip generation of microbubbles as a practical technology for manufacturing contrast agents for ultrasonic imaging" by Kanaka Hettiarachchi, Esra Talu, Marjorie L. Longo, Paul A. Dayton and Abraham P. Lee Lab on a Chip, 2007, 7, 463-468. Provided is the soft molded PDMS (silicone) based micro flow chamber below. An aspect of the present invention may utilize some aspects. An embodiment of the present invention provides a segment of a device that easily fits at the tip of a catheter. This approach has many features and characteristics:

1. Increased versatility—can vary shell composition (i.e. potentially drug/gene payload and concentration "on the fly");
2. Enables otherwise unfeasible bubbles. Making the bubbles at the tip means that stability problems are mitigated. The bubbles only have to survive a few seconds before therapeutic delivery. This may enable less stable chemical formulations or less stable bubble (i.e. shell/gas) permutations. Currently, gas is limited to one with very low rate of diffusion (i.e. high molecular weight). The new design enables the use of new gases or light gases at a minimum. This area isn't properly explored yet in our opinion.
3. Existing problems with bubble stability that require complex handling are circumvented.

Still referring FIG. 13, FIG. 13 provides a schematic plan view of the microfluidic flow-focusing device or in-situ device. The microfluid device may be less than about 1 mm and therefore can be fit inside a catheter for example. The arrows indicate direction of flow of liquid inlet(s) and gas inlet.

It should be appreciated that the widths and heights may be larger or smaller as required. The contours and shapes may vary as well.

Figure 14A:
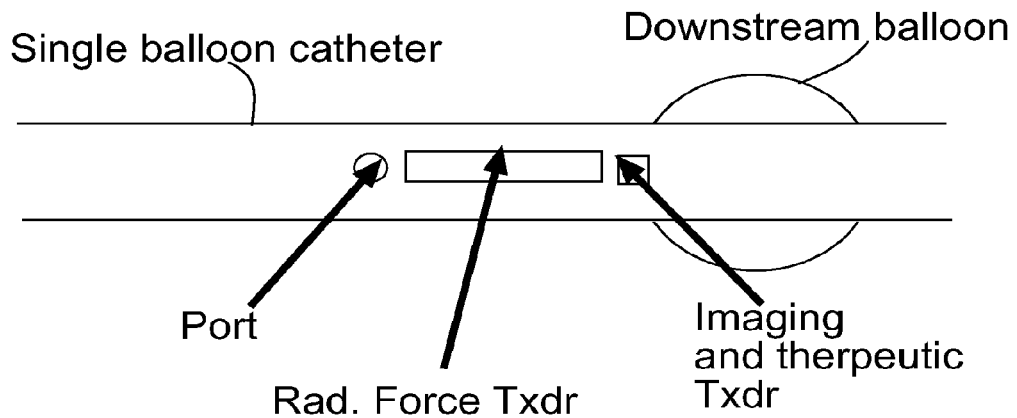
FIGS. 14(A)-(B) provide a schematic elevation view of embodiments of the catheter system having occlusion or sealing systems.

FIG. 14(A) provides a schematic elevational view of an embodiment (or partial embodiment) or approach of the present invention that provides a single occlusion balloon to temporally stop flow—distal to transducer and drug bubble port. The balloon may be released (or partially released) after procedure (or during the procedure) and drug bubble residual or other medium flows systemically or as available.

Figure 14B:
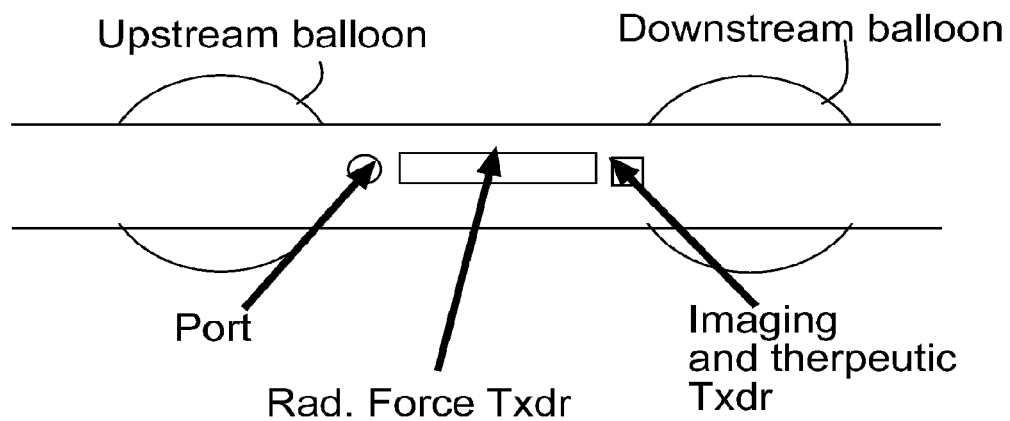

FIG. 14(B) provides an embodiment similar to device as shown in FIG. 14(A), however the instant embodiment or approach of the present invention provides a dual occlusion balloon to stop flow (or hinder flow) and create a sealed vessel section (or partially sealed section) in which drug (or applicable medium) is injected, delivered and then flushed to eliminate systemic delivery concerns. The instant approach may also include second port well separated from first so as to permit flush in from one and vacuum out at other—i.e. ports upstream and downstream and close to each of the balloons (or located as desired or required).

The balloons may be any available sealing, occluding or blocking designs, structure, or devices available to those skilled in the art (or so as to provide partial occlusion when applicable or desired).

Examples of balloon (or occlusion) related catheter devices and associated methods are provided below. The following patents, applications and publications as listed below are hereby incorporated by reference in their entirety herein. The devices, systems, and methods of various embodiments of the invention disclosed herein may utilize aspects disclosed in the following references, applications, publications and patents and which are hereby incorporated by reference herein in their entirety:

1. U.S. Pat. No. 6,626,861, Sep. 30, 2003, "Balloon catheter apparatus and method", Hart, et al.
2. U.S. Patent Application Publication No. 2006/0235501, Oct. 19, 2006, "Stent supplying device", Igaki, et al.
3. U.S. Patent Application Publication No. 2007/0055132, Mar. 8, 2007, "Catheter device," Camus, et al.

4. U.S. Pat. No. 5,868,708, Feb. 9, 1999, "Balloon catheter apparatus and method", Hart, et al.

5. U.S. Patent Application Publication No. 2006/0189928, Aug. 24, 2006, "Catheter device", Camus, et al.

6. U.S. Patent Application Publication No. 2008/0243233, Oct. 2, 2008, "Device and Methods for Treatment of Vascular Bifurcations", Ben-Muvhar, et al.

7. U.S. Pat. No. 5,222,970, Jun. 29, 1993, "Method of and system for mounting a vascular occlusion balloon on a delivery catheter", Reeves, et al.

8. U.S. Pat. No. 5,707,354, Jan. 13, 1998, "Compliant catheter lumen and methods", Salmon, et al.

9. U.S. Patent Application Publication No. 2003/0163192, Aug. 28, 2003, "Methods for vascular reconstruction of diseased arteries", Wallace, et al.

10. U.S. Patent Application Publication No. 2002/0169496, Nov. 14, 2002, "Methods for vascular reconstruction of diseased arteries", Wallace, et al.

11. U.S. Patent Application Publication No. 2008/0103443, May 1, 2008, "Balloon catheter for treating hardened lesions", Kabrick, et al.

12. U.S. Pat. No. 6,565,601, May 20, 2003, "Methods for vascular reconstruction of diseased arterie, Wallace, et al.

13. U.S. Pat. No. 5,827,171, Oct. 27, 1998, 'Intravascular circulatory assist device", Dobak, et al.

14. U.S. Pat. No. 7,011,677, Mar. 14, 2006, "Methods for vascular reconstruction of diseased arteries", Wallace, et al.

15. U.S. Pat. No. 5,941,870, Aug. 24, 1999, "Catheter system having a balloon angioplasty device disposed over a work element lumen", Jang, et al.

16. U.S. Patent Application Publication No. 2004/0158308, Aug. 12, 2004, "Delivery catheter for ribbon-type prosthesis and methods of use", Hogendijk, et al.

17. U.S. Patent Application Publication No. 2006/0161103, "Catheter systems and methods for their use in the treatment of calcified vascular occlusions", Constantz, et al.

18. U.S. Patent Application Publication No. 2003/0199820, Oct. 23, 2003, "Catheter systems and methods for their use in the treatment of calcified vascular occlusions", Constantz, et al.

19. U.S. Patent Application Publication No. 2002/0044907, Apr. 18, 2002, "Catheter systems and methods for their use in the treatment of calcified vascular occlusions", Constantz, et al.

20. U.S. Patent Application Publication No. 2007/0049867, "System for treating chronic total occlusion caused by lower extremity arterial disease", Shindelman, et al.

21. U.S. Pat. No. 5,041,089, Aug. 20, 1991, "Vascular dilation catheter construction", Mueller, et al.

22. U.S. Pat. No. 5,755,707, May 26, 1998, "Vascular dilating catheter", Miyagawa, et al.

23. U.S. Patent Application Publication No. 2004/0111145, Jun. 10, 2004, "Vascular prosthesis for the treatment of abdominal aortic aneurysms, using a combined laparoscopic/open and endovascular technique, and delivery system for releasing a prosthesis fitted with anchoring stents", Serino, et al.

24. U.S. Patent Application Publication No. 2007/0043389, Feb. 22, 2007, "System for treating chronic total occlusion caused by lower extremity arterial disease", Shindelman, et al.

25. U.S. Patent Application No. 2003/0220666, Nov. 27, 2003, "Solid embolic material with variable expansion", et al.

26. U.S. Pat. No. 5,117,831, Jun. 2, 1992, "Vascular catheter having tandem imaging and dilatation components", Jang, et al.

27. U.S. Pat. No. 6,527,979, Mar. 4, 2003, "Catheter systems and methods for their use in the treatment of calcified vascular occlusions", Constantz, et al.

28. U.S. Pat. No. 5,447,503, Sep. 5, 1995, "Guiding catheter tip having a tapered tip with an expandable lumen", Miller, et al.

29. U.S. Pat. No. 7,198,637, Apr. 3, 2007, "Method and system for stent retention using an adhesive", Deshmukh, et al.

30. U.S. Pat. No. 5,415,634, May 16, 1995, "Catheter having helical inflation lumen", Glynn, et al.

Characteristics and Features that May be Implemented in Whole or in Part (in any Permutation) with the Various Embodiments or Partial Embodiments as Discussed Throughout this Document An embodiment or approach of the present invention provides Dual use IVUS provides imaging plus therapy.

An embodiment or approach of the present invention provides Rapamycin bubbles (and other drugs with therapeutic effect—primarily antiproliferative but could be others—including dual drug use—such as one drug to precondition tissue for a second drug to operate with efficacy).

Gene Bubbles

An embodiment or approach of the present invention provides the use of cell-specific promoter constructs to target gene expression specifically to one or multiple cell types in combination or independently. This includes but is not limited to endothelial cell specific promoters (e.g. Tie-2, eNos), smooth muscle cell specific promoters (e.g. SMMHC, SM alpha-actin, SM22-alpha, myocardin), macrophages (e.g. mac-1) and promoter of these genes that have been modified by mutating specific cis DNA sequences so as to limit inhibition of the promoter and increase activity. An example would be, but not limited, to a G/C mutation in the SM22a promoter which renders the promoter active in all smooth muscle cell phenotypes [e.g., Wamhoff et al, Circ Res, 2004]. Genes under control of a tissue selective promoter include but are not limited to anti-proliferative genes such p21, p53, KLF4 and proliferative genes such as PCNA. In one scenario, a proliferative gene is targeted to endothelial cell to promote re-endothelialization and an anti-proliferative gene is targeted to smooth muscle to prevent restenosis.

An embodiment or approach of the present invention provides molecular targeted bubbles (VCAM-1, PECAM, etc.). The targeting can be in context of diagnosis or therapeutic use of bubbles—or both. The targeting to be any disease with molecular marker on endothelial surface. For example, VCAM-1 for atherosclerotic plaque—including "vulnerable plaque" or $\alpha_\omega\beta_3$ for angiogenesis associated with cancer.

An embodiment or approach of the present invention provides radiation force and bubbles (which usually involves long pulse bursts, but not necessarily).

An embodiment or approach of the present invention provides IVUS catheter with drug bubble delivery port upstream.

An embodiment or approach of the present invention provides drug delivery "port" is plural and forms an annulus.

An embodiment or approach of the present invention provides a mechanically scanned single element transducer—mechanically scanning achieves the regional coverage.

An embodiment or approach of the present invention provides phased array transducer—side fire/annular fire. The phased array may be used for imaging and therapy.

An embodiment or approach of the present invention provides a combination transducer elements—high power/low frequency, low power high frequency.

An embodiment or approach of the present invention provides different transducer elements in different formats—e.g. phased array imaging plus scanned single element therapeutic.

An embodiment or approach of the present invention provides a single occlusion balloon to temporally stop flow—distal to transducer and drug bubble port (for instance, release balloon after procedure and drug bubble residual flows systemically).

An embodiment or approach of the present invention provides a dual occlusion balloon to stop flow and create a sealed vessel section in which drug is injected, delivered and then flushed to eliminate systemic delivery concerns (requires second port well separated from first so as to permit flush in from one and vacuum out at other—i.e. ports upstream and downstream and close to each of the balloons)

An embodiment or approach of the present invention provides a 3D scanning to record extent of problem lesion followed by automated 3D sweep across the lesion to achieve therapeutic effect—i.e. it may be time/procedure efficient for the physician to outline the 3D extent of the plaque and then have the system sweep the region by way of automated sequence of 1D lines to fully encompass the 2D surface of the 3D lesion. The "Track back" method, well known in IVUS, can be used "TrakBackII" from Volcano Corp for their array IVUS.

An embodiment or approach of the present invention provides a vulnerable plaque application as mentioned immediately above, except application is diagnosis of vulnerable plaque. (Further, it doesn't actually doesn't have to be 3D—but 3D is typically best). The means of differentiating vulnerable plaque comprises—any permutation of:
  a. Using appropriate molecular targeted microbubbles (VCAM-1 for example).
  b. Using microbubbles to detect microvasculature of vasa vasorum—an indicator of active vulnerable plaque (see for example, see reference Dutch group—Goertz, van der Steen et al. http://publishing.cur.nl/ir/rcpub/assct/7950/060908_Frijlink,%20Martijn%20Egbert.pdf, Harmonic Intravascular Ultrasound Thesis, Martijn Frijlink, 2006 Delft, Netherlands).
  c. Performing signal processing (attenuation/frequency vs. depth as per "virtual histology" of Volcano (Vince et al.)
  d. Performing an elasticity based measurement to detect unusual softness of plaque (e.g., per known methods of transducer inside balloon described by M O'Donnell or measuring tissue response to pulsatile blood forces—Van Der Steen)
  e. "Tissue thermal strain imaging": Identification of vulnerable atherosclerotic plaque using IVUS-based thermal strain imaging: Yan Shi; Witte, R. S.; O'Donnell, M.; *Ultrasonics, Ferroelectrics and Frequency Control, IEEE Transactions* in Volume 52, Issue 5, May 2005 Page(s):844-850

An embodiment or approach of the present invention sets forth to stabilize the vulnerable plague by delivery compounds such as basic FGF which promoter smooth muscle proliferation and migration to stabilize the weak fibrous cap. We will refer to all analogous therapy approaches for treating brain aneurysms with cerebral micro-coils. Micro-coils are delivered to the blood vessel wall where an aneurysm occurred to provide support for smooth muscle to proliferate and migrate and heal the aneurysm. An approach or embodiment promote, in the case, smooth muscle proliferation and migration, not inhibit it.

An embodiment or approach of the present invention provides a transducer(s) that may include any permutation of the following:
  a. Single element capable of any or all of: radiation force, imaging, bubble rupture.
  b. Phased array (in any format: longitudinal or annular) capable of any or all of: radiation force, imaging, bubble rupture.
  c. Either or above wherein element(s) are dual (or triple) layer arranged to provide (typically) high power at lower frequency and lower power/fine resolution using high frequency.
  d. Wherein the different transducers performing different functions are not arranged one over the other. Place an elongated radiation force transducer (or array) upstream of imaging/delivery zone (see figure). Then have an imaging transducer—imaging the bubbles that have been pushed to the zone of interest. Then have a delivery transducer. (Subsets also possible—such as dedicated elongated radiation force transducer plus combined imaging/delivery transducer (or array).
  e. An embodiment or approach of the present invention provides a transducer(s) that can be formed from piezoelectric material (preferably ceramic but could be piezoelectric polymer PVDF). Alternatively transducers can be electrostatic, silicon (or other material) "MEMS" devices.

An embodiment or approach of the present invention provides a method for localized delivery of drug from drug loaded microbubbles using high intensity ultrasound wherein the location of the focal delivery is guided by an integral, real-time, coincident, ultrasound imaging system.

An embodiment (or partial embodiment) or approach of the present invention provides a method for localized drug delivery wherein the drug coated bubbles possess a selected molecular attachment ligand—such as VCAM-1, P-Selectin, etc. under realtime ultrasound image guidance, such as:
  dual targeting method—fast catch/slow hold
  variant on bubbles such as liposomes
  nanoparticle+bubble
  dual modality contrast Ultrasound+MRI contrast Bubble+ferrous
  potential of drug not being integrated in bubble shell but existing in free solution aside the bubbles and relying on bubble related sonoporation to result in preferential drug uptake.

An embodiment or approach of the present invention provides a drug that is rapamycin (antiproliferative, immunosuppressive, or antiinflammatory drug, such as rapamycin, tacrolimus, paclitaxel, dexamethasone, or an active analog or derivative, or combinations thereof). The drug may be selected from a group comprising actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, Gleevec, wortmannin, PDGF inhibitors, AG1295, rho kinase inhibitors, Y27632, calcium channel blockers, TRAM-34, IKCa channel blockers, amlodipine, nifedipine, and ACE inhibitors, S1P1 and/or S1P3 receptor antagonists, sphingosine kinase 1 inhibitors, synthetic polysaccharides, ticlopinin, dipyridamolc, clopidogrcl, fondaparinux, streptokinase, urokinase, r-urokinase, r-prourokinase, rt-PA, APSAC, TNK-rt-PA, reteplase, alteplase, monteplase, lanoplase, pamiteplase, staphylokinase, abciximab, tirofiban, orbofiban, xemilofiban, sibrafiban, roxifiban, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radio-isotope, a prodrug, antibody fragments, antibodies, gene therapy agents, viral vectors and plasmid DNA vectors.

An embodiment or approach of the present invention provides a subset of relevant bubble properties—dimensions, core gas, shell materials, etc. and including oily shell—decafluorobutane An embodiment or approach of the present invention provides an acoustic radiation force that may be used to translate bubbles towards a selected vessel wall.

An embodiment or approach of the present invention provides microbubbles are targeted to blood vessels that routinely undergo and angioplasty and/or stenting (including balloon expansion stents and self-expanding stents), including but not limited to the coronary arteries, coronary artery branch points, carotid arteries, cerebral arteries, femoral arteries.

An embodiment or approach of the present invention provides a systemic injection of bubbles.

An embodiment or approach of the present invention provides a localized injection of bubbles—from catheter tip—preferably same catheter as imaging but potentially from separate one. See catheter cross-sectional drawing above.

An embodiment or approach of the present invention provides an ultrasound image guidance of bubbles in a highly bubble-specific mode using one of pulse inversion, amplitude scaling ("power modulation") or combination of two ("contrast pulse sequences").

An embodiment or approach of the present invention provides an ultrasound intensity has therapeutic (drug delivery) effect, wherein ultrasound has cell death effect.

An embodiment or approach of the present invention provides the uses of a ultrasound catheter—about 1-about 2 MHz therapeutic, about 30 MHz imaging.

An embodiment or approach of the present invention provides a co-located transducer—imaging device overlaying the therapeutic device, imaging device residing in an aperture formed within center of therapeutic device (less desirable than overlaying).

An embodiment or approach of the present invention provides a synchronized operation—the imaging system is "gated" to never operating during the time of therapeutic operation.

An embodiment or approach of the present invention provides a therapeutic system "listens" for imaging system operation and inserts therapeutic pulses between imaging operations.

An embodiment or approach of the present invention provides an imaging system "listens" for therapeutic system operation and inserts imaging pulses between therapeutic operations.

An embodiment or approach of the present invention provides a "Pulse sequence" claims—X seconds (s) of therapeutic, followed by Y s of imaging, and so on for Z minutes.

An embodiment or approach of the present invention provides an integrating of this device on a catheter with other preferred catheter device options—e.g. balloon, pressure measurement, temperature measurement, blood sampling.

An embodiment or approach of the present invention provides a catheter with "over the wire" capability—the standard—has capability to be "threaded" over an in-place metal wire.

An embodiment or approach of the present invention provides a catheter that may be a derivative of the "Volcano" IVUS catheter (phased annular array). A therapeutic transducer—side firing—is placed near to the imaging annular array.

An embodiment or approach of the present invention provides a catheter that may be related to some extent to the "Boston-Scientific" IVUS catheter (mechanically scanned single element) i.e. the existing high frequency transducer element is replaced with a stack of low frequency (therapeutic) 1 MHz element with 30 MHz imaging overlaid. Alternatively, there are two transducers side by side in close proximity.

An embodiment or approach of the present invention provides a catheter possessing an imaging transducer/array in any one or more of the following formats: single element transducer rotated in circumferential fashion to form coronal plane, circumferential array forming coronal plane, side-fire array and wherein the therapeutic array is in any one of more of the following formats: single element transducer rotated in circumferential fashion to form coronal plane, circumferential array forming coronal plane, side-fire array An embodiment or approach of the present invention provides an imaging transducer/array is in any one or more of the following formats: single element transducer rotated in annular fashion to form coronal plane, annular array forming coronal plane, side-fire array and wherein the therapeutic transducer is single focused element or annular array.

An embodiment or approach of the present invention provides a pro-proliferative for filling up an aneurysm, occlusive treatment upstream of an angiogenic region associated with evolving cancer; Image guidance other than ultrasound; or other mechanisms for therapeutic delivery—such as heat as opposed to acoustic disruption.

Wherein the image guidance (other than ultrasound) includes one or more of: 1) X-ray and its derivatives (plain X-ray, realtime fluoroscopy and computed tomography [CT]), or 2) Magnetic Resonance Imaging (MRI)

An embodiment or approach of the present invention provides a complementary drug operation—two drugs in different bubble populations that are stable in isolation but upon ultrasound disruption mix and become active/unstable/therapeutic.

An embodiment or approach of the present invention provides a therapeutic ultrasound plus bubble, drug and stent—wherein ultrasound induces vibrational mode/activity within stent so as to elicit therapeutic effect among cells/drugs/bubbles adjacent to stent surface.

An embodiment or approach of the present invention provides a different types of stent and different generations of stent—bare metal stent, current DES, dissolving polymer stent, non polymer stent.

An embodiment or approach of the present invention provides an acoustic signature of stent that may be monitored to determine degree of accumulation of stiff acoustic loading on stent and any change resulting from therapeutic effect.

An embodiment or approach of the present invention provides microbubbles that are delivered to a vascular aneurism to deliver a drug that promotes smooth muscle migration and proliferation to heal the aneurism. Drugs include but are not limited to PDGF-BB, bFGF, etc.

An embodiment or approach of the present invention provides a method for localized drug delivery wherein the drug-carrying bubbles possess a selected molecular attachment ligand—such as VCAM-1, P-Selectin, etc. under real-time ultrasound image guidance including any permutation thereof:

dual targeting method—fast catch/slow hold [52]

3. microbubble composition, for use as in claims 1 and 2 such that a plurality of targeting ligands capable of binding with the diseased tissue, some of the ligands capable of binding rapidly, and others binding firmly, are attached to the microbubbles.

variant on bubbles such as liposomes nanoparticle+bubble

Microbubble composition, such as in claim 1, 2 or 3, having liposomes or biocompatible nanoparticles applied to the microbubble shell to house the drug compounds to be released by targeted insonation dual modality contrast Ultrasound+MRI contrast Bubble+ ferrous (or in another disclosure)

potential of drug not being integrated in bubble shell but existing in free solution aside the bubbles and relying on bubble related sonoporation to result in preferential drug uptake.

An embodiment or approach of the present invention provides a drug that may be rapamycin ((antiproliferative, immunosuppressive, or antiinflammatory drug, such as rapamycin, tacrolimus, paclitaxel, dexamethasone, or an active analog or derivative, or combinations thereof).

An embodiment or approach of the present invention provides a subset of relevant bubble properties—dimensions, core gas, shell materials, etc.

An embodiment or approach of the present invention provides a microbubble composition having drug incorporated, situated, dispersed, dissolved therein directly in the shell, core or core multiplicity, or attached to the outside of the shell, having shell(s) comprised with lipids, phospholipids, oils, fats, lipopolymers, polymers, proteins, surfactants or combinations thereof, shell thickness varied from monomolecular 1 nm, to multimolecular and multilamellar, up to and including 1000 nm.

An embodiment or approach of the present invention provides microbubble compositions having internal core filled with the gas, gas-vapor mixture or gas precursor phase, gas having molecular mass from about 10 to about 360.

An embodiment or approach of the present invention provides a microbubble compositions having decafluorobutane core.

An embodiment or approach of the present invention provides an acoustic radiation force is used to translate bubbles towards a selected vessel wall, or other organs or tissues as desired.

An embodiment or approach of the present invention provides an application in the coronary artery, application in other vessels, or other organs or tissues as desired.

An embodiment or approach of the present invention provides a systemic injection of bubbles.

An embodiment or approach of the present invention provides a localized injection of bubbles—from catheter tip—preferably same catheter as imaging but potentially from separate one. See catheter cross-sectional drawing above.

An embodiment or approach of the present invention provides an ultrasound image guidance of bubbles in a highly bubble-specific mode using one of pulse inversion, amplitude scaling ("power modulation") or combination of two ("contrast pulse sequences"):

wherein ultrasound intensity has therapeutic (drug delivery) effect; and/or wherein ultrasound has cell death effect.

An embodiment or approach of the present invention provides an ultrasound catheter—1-2 MHz therapeutic, 30 MHz imaging.

An embodiment or approach of the present invention provides a co-located transducer—imaging device overlaying the therapeutic device, imaging device residing in an aperture formed within center of therapeutic device (which may be less desirable than overlaying).

An embodiment or approach of the present invention provides a synchronized operation—the imaging system is "gated" to never operating during the time of therapeutic operation:

wherein the therapeutic system "listens" for imaging system operation and inserts therapeutic pulses between imaging operations, and/or wherein the imaging system "listens" for therapeutic system operation and inserts imaging pulses between therapeutic operations.

An embodiment or approach of the present invention provides a "Pulse sequence" claims—X seconds(s) of therapeutic, followed by Y s of imaging, and so on for Z minutes (time, repetition, cycles and duration as desired or required).

An embodiment or approach of the present invention provides an integrating of this device on a catheter with other preferred catheter device options—e.g. balloon, pressure measurement, temperature measurement, blood sampling.

An embodiment or approach of the present invention provides a catheter with "over the wire" capability—the standard—has capability to be "threaded" over an in-place metal wire.

An embodiment or approach of the present invention provides a catheter that is a derivative of the "Volcano" IVUS catheter (phased annular array). A therapeutic transducer—side firing—is placed near to the imaging annular array.

An embodiment or approach of the present invention provides a catheter that is a derivative of the "Boston-Scientific" IVUS catheter (mechanically scanned single element) i.e. the existing high frequency transducer element is replaced with a stack of low frequency (therapeutic) about 1 MHz element with about 30 MHz imaging overlaid. Alternatively, there are two transducers side by side in close proximity. Frequency may vary as desired or required.

REFERENCES CITED

The following patents, applications and publications as listed below are hereby incorporated by reference in their entirety herein. The devices, systems, and methods of various embodiments of the invention disclosed herein may utilize aspects disclosed in the following references, applications, publications and patents and which are hereby incorporated by reference herein in their entirety:

1. U.S. Pat. No. 7,078,015, Unger, "Ultrasound Imaging and Treatment", Jul. 18, 2006.

2. U.S. Patent Application Publication No. 2005/017725 A1, Hunter, William L., et. al., "Medical Implants and Anti-Scarring Agents", Aug. 11, 2005.

3. U.S. Patent Application Publication No. 2002/0082680 A1, Shanley, John F., et. al., "Expandable Medical Device for Delivery of Beneficial Agent", Jun. 27, 2002.

4. U.S. Patent Application Publication No. 2003/0181973 A1, Sahota, Harvinder, "Reduced Restinosis Drug Containing Stents", Sep. 25, 2003.

5. U.S. Patent Application Publication No. 2003/0206960 A1, Iversen, Patrick L., et. al., "Delivery of Microparticle-Conjugated Drugs for Inhibition of Stenosis", Nov. 6, 2003.

6. U.S. Patent Application Publication No. 2003/0207907 A1, Iversen, Patrick L., et. al., "Delivery of Microparticle-Conjugated Drugs for Inhibition of Stenosis", Nov. 6, 2003.

7. U.S. Patent Application Publication No. 2004/0077948 A1, Violante, Michael R., "Echogenic Coatings with Overcoat", Apr. 22, 2004.

8. U.S. Patent Application Publication No. 2004/0126400 A1, Iverson, Patrick L., et. al., "Delivery of Therapeutic Compounds Via Microparticles or Microbubbles", Jul. 1, 2004.

9. U.S. Patent Application Publication No. 20040236414, Brar, Balbir S., et. al., "Devices and Methods for Treatment of Stenotic Regions", Nov. 25, 2004.

10. U.S. Patent Application Publication No. 2004/0254635 A1, Shanley, John F., et. al., "Expandable Medical Device for Delivery of Beneficial Agent", Dec. 16, 2004.

11. U.S. Patent Application Publication No. 2007/0010577 A1, Lanza, Gregory, M., et. al., "Targeted Atherosclerosis Treatment", Jan. 11, 1007.

12. U.S. Patent Application Publication No. 2007/0003528 A1, Consigny, Paul, et. al., "Intracoronary Device and Method of Use Thereof", Jan. 4, 2007.

13. U.S. Pat. No. 6,409,667, Hossack, et. al., "Medical Diagnosis Ultrasound Transducer System and Method for Harmonic Imaging", Jun. 25, 2002.

14. U.S. Pat. No. 7,341,569 to Soltani, et al., "Treatment of Vascular Occlusions Using Ultrasonic Energy and Microbubbles", Mar. 11, 2008.

15. U.S. Pat. No. 5,770,222 to Unger, et al., "Therapeutic Drug Delivery Systems", Jun. 23, 2008.

16. PCT International Application No. Serial No. PCT/US2008/056643, filed Mar. 12, 2008, entitled, "Access Needle Pressure Sensor Device and Method of Use,"

17. PCT International Application No. Serial No. PCT/US2008/056816, filed Mar. 13, 2008, entitled, "Epicardial Ablation Catheter and Method of Use,"

18. PCT International Application No. Serial No. PCT/US2008/057626, filed Mar. 20, 2008, entitled, "Electrode Catheter for Ablation Purposes and Related Method Thereof,"

REFERENCES CITED

The following patents, applications and publications as listed below and throughout this document are hereby incorporated by reference in their entirety herein. The devices, systems, and methods of various embodiments of the invention disclosed herein may utilize aspects disclosed in the following references, applications, publications and patents and which are hereby incorporated by reference herein in their entirety:

Literature Cited

1. Thom, T., et al., *Heart disease and stroke statistics—2006 update: a report from the American Heart Association Statistics Committee and Stroke Statistics Subcommittee.* CIRCULATION, 2006. 113(6): p. e85-e151.

2. Kandzari, D. E., et al., *Frequency, Predictors, and Outcomes of Drug-Eluting Stent Utilization in Patients With High-Risk Non-ST-Segment Elevation Acute Coronary Syndromes.* the American Journal of Cardiology, 2005. 96(6): p. 750-755.

3. Rao, S. V., et al., *On-Versus Off-Label Use of Drug-Eluting Coronary Stents in Clinical Practice (Report from the American College of Cardiology National Cardiovascular Data Registry [NCDR]).* The American Journal of Cardiology, 2006. 97(10): p. 1478-1481.

4. FDA, *Circulatory Systems Devices Advisory Panel,* 7-8 December, 2006. Transcript:http://www.accessdata.fda-.gov/scripts/cdrh/cfdocs/cfAdvisory/details.cfm-?mtg=672, 2006.

5. Hendrix, J., et al., *5' CArG degeneracy in smooth muscle {alpha}-actin is required for injury-induced gene suppression in vivo.* J. Clin. Invest., 2005. 115(2): p. 418-427.

6. McDonald, O., et al., *Control of SRF binding to CArG box chromatin regulates smooth muscle gene expression in vivo.* J. Clin. Invest., 2006. 116(1): p. 36-48.

7. Owens, G., M. Kumar, and B. Wamhoff, *Molecular Regulation of Vascular Smooth Muscle Cell Differentiation in Development and Disease.* Physiol. Rev., 2004. 84(3): p. 767-801.

8. Wamhoff, B., et al., *L-type Voltage-Gated Ca2+ Channels Modulate Expression of Smooth Muscle Differentiation Marker Genes via a Rho Kinase/Myocardin/SRF-Dependent Mechanism.* Circulation Research, 2004. 95(4): p. 406-414.

9. Braun, M., et al., *Cellular adhesion molecules on vascular smooth muscle cells.* Cardiovascular Research, 1999. 41(2): p. 395-401.

10. Braun-Dullaeus, R., et al., *Cell cycle-dependent regulation of smooth muscle cell activation.* Arterioscler Thromb Vasc Biol, 2004. 24: 845-850, 2004: p. 845-850.

11. Landry, D., et al., *Activation of the NF-kappa B and I kappa B system in smooth muscle cells after rat arterial injury. Induction of vascular cell adhesion molecule-1 and monocyte chemoattractant protein-1.* Am J Pathol, 1997. 151(4): p. 1085-1095.

12. Parry, T., et al., *Drug-eluting stents: sirolimus and paclitaxel differentially affect cultured cells and injured arteries.* Eur J Pharmacol, 2005. 524(1-3): p. 19-29.

13. Wessely, R., A. Schomig, and A. Kastrati, *Sirolimus and Paclitaxel on Polymer-Based Drug-Eluting Stents: Similar But Different.* Journal of the American College of Cardiology, 2006. 47(4): p. 708-714.

14. Webster, A., et al., *Target of rapamycin inhibitors (sirolimus and everolimus) for primary immunosuppression of kidney transplant recipients: a systematic review and meta-analysis of randomized trials.* Transplantation, 2006. 81(9): p. 1234-1248.

15. Ross, R., *The pathogenesis of atherosclerosis: a perspective for the 1990s.* Nature, 1993. 362: p. 801-809.

16. Denger, T. and T. Pober, *Cellular and molecular biology of cardiac transplant rejection.* Journal of Nuclear Cardiology, 2000. 7: p. 669-685.

17. Sheridan, F., P. Cole, and D. Ramage, *Leukocyte adhesion to the coronary microvasculature during ischemia and reperfusion in an in vivo canine model.* CIRCULATION, 1996. 93: p. 1784-1787.

18. Villanueva, F., A. Klibanov, and W. Wagner, *Microbubble-endothelial cell interactions as a basis for assessing endothelial function.* ECHOCARDIOGRAPHY, 2002. 19: p. 427-438.

19. Klibanov, A. L., *Targeted Delivery of Gas-Filled Microspheres, Contrast Agents for Ultrasound Imaging.* Advanced Drug Delivery Reviews, 1999. 37: p. 139-157.
20. Klibanov, A., et al., *Targeted ultrasound contrast agent for molecular imaging of inflammation in high-shear flow.* Contrast Media and Molecular Imaging, 2006. 1(6): p. 259-266.
21. Rosenschein, U., et al., *Ultrasound Imaging-Guided Noninvasive Ultrasound Thrombolysis.* CIRCULATION, 2000. 102: p. 238.
22. Unger, E. and D. Yellohair, *Methods and apparatus for performing diagnostic and therapeutic ultrasound simultaneously* U.S. Pat. No. 5,558,092, 1996.
23. Chan, *An image-guided high intensity focused ultrasound device for uterine fibroids treatment.* Medical Physics, 2002. 29(11): p. 2611-20.
24. Vaezy, S., et al., *Ultrasound image-guided therapy.* Academic Radiology, 2003. 10(8): p. 956.
25. Vaezy, S., et al., *High intensity focused ultrasound for hemostasis of femoral artery catheter wounds.* Ultrasound in Medicine and Biology, 2006. 32(5 Supplement 1): p. 100.
26. Crum, L., *Guided High Intensity Focused Ultrasound (HIFU) for Mission-Critical Care.* http://www.nsbri.org/Research/Projects/viewssummary.epl?pid=133, 2004.
27. Bouakaz, A., F. Cate, and N. de Jong, *A new ultrasonic transducer for improved contrast nonlinear imaging.* Physics in Medicine & Biology, 2004. 49(16): p. 3515-3525.
28. Forsberg, F., et al., *Design and acoustic characterization of a multi-frequency harmonic array for nonlinear contrast imaging.* Proceeding of 2001 IEEE Ultrasonics Symposium, 2001. 2: p. 1721-1724.
29. Rychak, J., A. Klibanov, and J. Hossack, *Acoustic Radiation Force Enhances Targeted Delivery of Ultrasound Contrast Microbubbles: In vitro Verification.* IEEE Transactions on Ultrasonics Ferroelectrics & Frequency Control, 2005. 52(3): p. 421-433.
30. Marx, S., et al., *Rapamycin-FKBP Inhibits Cell Cycle Regulators of Proliferation in Vascular Smooth Muscle Cells.* Circulation Research, 1995. 76(3): p. 412-417.
31. Klibanov, A., et al., *Attachment of ligands to gas-filled microbubbles via PEG spacer and lipid residues anchored at the interface.* Proc. Intl. Symp. Control. Rel. Bioact. Mat., 1999. 26: p. 124-125.
32. Wilson, T., et al., *The ultrasonix 500RP: A commercial ultrasound research interface.* IEEE Transactions Ultrasonics, Ferroelectrics and Frequency Control, 2006. 53(10): p. 1772-1782.
33. Takalkar, A., et al., *Binding and detachment dynamics of microbubbles targeted to P-selectin under controlled shear flow.* Journal of Controlled Release, 2004. 96(3): p. 473-482.
34. Klibanov, A., et al., *Detection of individual microbubbles of an ultrasound contrast agent: fundamental and pulse inversion imaging.* Academic Radiology, 2002: p. S279-S281.
35. Jayaweera, A., et al., *In vivo myocardial kinetics of air-filled albumin microbubbles during myocardial contrast echocardiography. Comparison with radiolabeled red blood cells.* Circulation Research, 1994. 74(6): p. 1157-1165.
36. Springer, T., *Adhesion receptors of the immune system.* Nature, 1990. 347: p. 425-434.
37. Dayton, P., et al., *Acoustic radiation force in vivo: a mechanism to assist targeting of microbubbles.* Ultrasound in Medicine & Biology, 1999. 25(8): p. 1195-1201.
38. Fowlkes, J., et al., *The role of acoustic radiation force in contrast enhancement techniques using bubble-based ultrasound contrast agents.* Journal of the Acoustical Society of America, 1993. 93: p. 2348.
39. Zhao, S., et al., *Radiation force assisted targeting facilitates ultrasonic molecular imaging.* Molecular Imaging, 2004. 3: p. 1-14.
40. Shortencarier, J., et al., *A method for radiation force localized drug delivery using gas-filled liposphseres.* IEEE Trans. Ultrasonics, Ferroelectrics and Frequency Control, 2004. 51: p. 822-831.
41. Dayton, P., et al., *A preliminary evaluation of the effects of primary and secondary radiation forces on acoustic contrast agents.* IEEE Transactions on Ultrasonics Ferroelectrics & Frequency Control, 1997. 44(6): p. 1264-1277.
42. Dayton, P., J. Allen, and K. Ferrara, *The magnitude of radiation force on ultrasound contrast agents.* Journal of the Acoustical Society of America, 2002. 112: p. 2183-2192.
43. Bosse, R. and D. Vestweber, *Only simultaneous blocking of the L- and P-selectin completely inhibits neutrophil migration into mouse peritoneum.* European Journal of Immunology, 1994. 24: p. 3019-3024.
44. Lindner, J., et al., *Ultrasound Assessment of Inflammation and Renal Tissue Injury With Microbubbles Targeted to P-Selectin.* CIRCULATION, 2001. 104(17): p. 2107-2112.
45. Burns, P., S. Wilson, and D. Simpson, *Pulse inversion imaging of liver blood flow: improved method for characterizing focal masses with microbubble contrast.* Invest Radiol., 2000. 35(1): p. 71.
46. BrockFisher, G. A., M. D. Poland, and P. G. Rafter, *Means for increasing sensitivity in non-linear ultrasound imaging systems* U.S. Pat. No. 5,577,505, 1996.
47. Phillips, P., *Contrast Pulse Sequences (CPS): Imaging non-linear microbubbles.* Proceedings of the 2001 IEEE Ultrasonics Symposium, 2001. 2: p. 1739-1745.
48. Klibanov, A., et al., *Proceedings of 26th International Symposium on Controlled Release of Bioactive Materials, Boston.* Controlled Release Society, 1999: p. 124-125.
49. Unger, E., et al., *Acoustically active lipospheres containing paclitaxel—A new therapeutic ultrasound contrast agent.* Investigative Radiology, 1998. 33: p. 886-892.
50. Boudennaia, T. Y. and K. L. Napoli, *Validation of a practical liquid chomatography with ultraviolet detection method for quantification of whole-blood everolimus in a clinical TDM laboratory.* Therapeutic Drug Monitoring, 2005. 27(2): p. 171-177.
51. Lindner, J. R., et al., *Ultrasound assessment of inflammation and renal tissue injury with microbubbles targeted to P-selectin.* Circulation, 2001. 104(17): p. 2107-2112.
52. Klibanov, A., et al., *Polymeric sialyl Lewis X microbubbles: targeted ultrasound contrast agents for molecular imaging of inflammation.* RSNA Abstract Book, 2006(Abs. # SSK06-06): p. 436-7.

It should be appreciated that various sizes, dimensions, contours, rigidity, shapes, flexibility and materials of any of the embodiments discussed throughout may be varied and utilized as desired or required It should be appreciated that the related components and subsystems discussed herein may can take on all shapes along the entire continual geometric spectrum of manipulation of x, y and z planes to provide and meet the anatomical and structural demands and requirements.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A method of providing therapy to a treatment site of a subject, said method comprising:
    advancing an ultrasound catheter to or in proximity to the subject's treatment site, said catheter having a proximal region and distal region;
    infusing microbubbles from said distal region of said ultrasound catheter into or proximal to the treatment site;
    administering a thrombus lysing agent to the subject's treatment site;
    delivering therapeutic ultrasonic energy, during said infusing, from within said distal region of said ultrasound catheter to said microbubbles to move said microbubbles, thereby focally delivering said microbubbles to or in proximity to the subject's treatment site; and
    providing real time imaging of the microbubbles as they are infused, wherein said microbubbles remain intact and echogenic as they are delivered to or in proximity to the subject's treatment site and are real time imaged;
    wherein said real time imaging is provided by delivering imaging ultrasonic energy from within said distal region of said ultrasound catheter to the treatment site.

2. The method of claim 1, wherein said thrombus lysing agent comprises a thrombus lysing drug.

3. The method of claim 2, wherein said thrombus lysing drug is selected from the group consisting of: rt-PA, APSAC, TNK-rt-PA, reteplase, alteplase, monteplase, lanoplase and pamiteplase.

4. The method of claim 1, wherein said thrombus lysing agent comprises a plasminogen activator.

5. The method of claim 1, wherein said providing real time imaging facilitates guidance of precise delivery of said microbubbles to the treatment site.

6. The method of claim 1, wherein the treatment site is in an artery and the thrombus lysing agent is administered intravenously.

7. The method of claim 1, wherein the thrombus lysing agent is administered from said distal region of said catheter.

8. The method of claim 7, wherein said thrombus lysing agent is administered side-by-side with the infusion of said microbubbles.

9. The method of claim 1 wherein the treatment site is in the cerebral vasculature.

10. The method of claim 9, wherein the treatment site is in a cerebral artery.

11. The method of claim 1, wherein the location of the focal delivery is guided by said real time imaging performed by an integral, real-time, coincident, ultrasound imaging system.

12. The method of claim 1, wherein the location of the focal delivery is guided by said real time imaging.

13. The method of claim 1, further comprising rupturing at least some of said microbubbles after moving said microbubbles to or in proximity to the subject's treatment site.

14. A system for providing therapy to a treatment site of a subject, the system comprising:
    a tubular member having a proximal region and distal region and a lumen, said distal region of said tubular member adapted to advance to or in proximity to the subject's treatment site;
    a microbubble reservoir in or in hydraulic communication with said lumen of said tubular member, said microbubble reservoir being adapted to release microbubbles that are intended to be located into or in proximity to the treatment site;

a thrombus lysing agent for delivery to the subject's treatment site;

a therapeutic ultrasound transducer at said distal region of said tubular member, said therapeutic ultrasound transducer configured to deliver therapeutic ultrasonic energy from within said distal region of said ultrasound catheter to said microbubbles to move, without rupturing, said microbubbles toward the treatment site;

a port in fluid communication with said lumen and opening to an external surface of said tubular member, said port being configured to release said microbubbles in a direction toward said therapeutic ultrasound transducer; and an imaging component comprising an imaging ultrasound transducer configured to provide real time imaging of said microbubbles as they are moved, wherein said imaging ultrasound transducer is mounted relative to said therapeutic ultrasound transducer at said distal region of said tubular member such that the delivery of said therapeutic ultrasound energy is aligned with said real time imaging.

15. The system of claim 14, wherein said tubular member is configured to be inserted into the cerebral vasculature.

16. The system of claim 14, further comprising a conduit configured to intravenously deliver said thrombus lysing agent, wherein the treatment site is an artery and wherein said tubular member is configured to be inserted within the artery.

17. The system of claim 16, wherein the treatment site is in a cerebral artery and said tubular member is configured to be inserted within the cerebral artery.

18. The system of claim 14, wherein the treatment site is in the cerebral vasculature.

19. The system of claim 18, wherein the thrombus lysing agent is selected from the group consisting of: rt-PA, APSAC, TNK-rt-PA, reteplase, alteplase, monteplase, lanoplase and pamiteplase.

20. The system of claim 14, wherein said therapeutic ultrasound transducer is further configured to deliver therapeutic ultrasonic energy from within said distal region of said ultrasound catheter to said microbubbles to rupture said microbubbles after moving said microbubbles toward the treatment site.

21. A method of providing therapy to a treatment site of a subject, said method comprising:

advancing an ultrasound catheter to or in proximity to the subject's treatment site, said catheter having a proximal region and a distal region;

infusing microbubbles from said distal region of said ultrasound catheter into or proximal to the treatment site;

administering a thrombus lysing agent to the subject's treatment site;

delivering therapeutic ultrasonic energy from within said distal region of said ultrasound catheter to said microbubbles to focally deliver said microbubbles to the treatment site; and delivering imaging ultrasonic energy from within said distal region of said ultrasound catheter to the treatment site to provide real time imaging of the treatment site;

wherein the microbubbles are infused directionally toward a location from which said therapeutic ultrasonic energy is directed.

22. A method of providing therapy to a treatment site of a subject, said method comprising:

advancing an ultrasound catheter to or in proximity to the subject's treatment site, said catheter having a proximal region and distal region;

infusing therapeutic material from said distal region of said ultrasound catheter;

delivering therapeutic ultrasonic energy from within said distal region of said ultrasound catheter to translate the therapeutic material so as to focally deliver said therapeutic material to the treatment site; and delivering imaging ultrasonic energy from within said distal region of said ultrasound catheter to the treatment site to provide real time imaging for guiding precise delivery of said therapeutic material to the treatment site.

23. The method of claim 22, further comprising controlling activation of said therapeutic ultrasonic energy.

24. The method of claim 22, wherein said treatment site comprises at least a portion of an organ.

25. The method of claim 24, wherein the organ is selected from the group consisting of: hollow organs, solid organs, parenchymal tissue, stromal tissue, and ducts.

26. The method of claim 22, wherein the treatment site comprises at least a portion of a tubular structure.

27. The method of claim 22, wherein said delivering therapeutic ultrasonic energy from said distal region of said ultrasound catheter to focally deliver said therapeutic material to the treatment site comprises delivering low frequency ultrasound energy to said therapeutic material.

28. The method of claim 22, wherein said therapeutic material is selected from the group consisting of: actinomycin-D, batimistat, c-myc antisense, dexamethasone, paclitaxel, taxanes, sirolimus, tacrolimus and everolimus, unfractionated heparin, low-molecular weight heparin, enoxaparin, bivalirudin, tyrosine kinase inhibitors, Gleevec, wortmannin, PDGF inhibitors, AG1295, rho kinase inhibitors, Y27632, calcium channel blockers, TRAM-34, IKCa channel blockers, amlodipine, nifedipine, and ACE inhibitors, S1P1 and/or S1P3 receptor antagonists, sphingosine kinase 1 inhibitors, synthetic polysaccharides, ticlopinin, dipyridamole, clopidogrel, fondaparinux, streptokinase, urokinase, r-urokinase, r-prourokinase, rt-PA, APSAC, TNK-rt-PA, reteplase, alteplase, monteplase, lanoplase, pamiteplase, staphylokinase, abciximab, tirofiban, orbofiban, xemilofiban, sibrafiban, roxifiban, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer) deferoxamine mesylate, a radiocontrast agent, a radio-isotope, a prodrug, antibody fragments, antibodies, gene therapy agents, viral vectors, and plasmid DNA vectors.

* * * * *